United States Patent
Ecker et al.

(10) Patent No.: US 6,208,900 B1
(45) Date of Patent: Mar. 27, 2001

(54) METHOD AND APPARATUS FOR RATE-RESPONSIVE CARDIAC PACING USING HEADER MOUNTED PRESSURE WAVE TRANSDUCER

(75) Inventors: Robert M. Ecker, Anoka; Lawrence C. McClure, Maple Grove; John D. Wahlstrand, Shoreview, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 106 days.

(21) Appl. No.: 08/623,477

(22) Filed: Mar. 28, 1996

(51) Int. Cl.⁷ .............................. A61N 1/362; A61N 1/365
(52) U.S. Cl. .................................. 607/17; 607/20
(58) Field of Search ........................ 607/18–20, 36–37, 607/17

(56) References Cited

U.S. PATENT DOCUMENTS

| | | | |
|---|---|---|---|
| 4,374,382 | 2/1983 | Markowitz | 607/27 |
| 4,485,813 | 12/1984 | Anderson | 607/122 |
| 4,556,063 | 12/1985 | Thompson | 607/32 |
| 4,702,253 | 10/1987 | Nappholz | 607/20 |
| 4,721,110 | 1/1988 | Lampadius | 607/20 |
| 4,763,646 | 8/1988 | Lekholm | 607/14 |
| 4,858,611 | * 8/1989 | Elliott | 607/20 |
| 4,884,576 | 12/1989 | Alt | 607/18 |
| 5,027,813 | * 7/1991 | Pederson et al. | 607/19 |
| 5,040,535 | * 8/1991 | Mann et al. | 607/19 |
| 5,052,388 | 10/1991 | Sivula | 607/30 |
| 5,063,927 | 11/1991 | Webb | 607/18 |
| 5,070,605 | 12/1991 | Daglow | 607/37 |
| 5,080,096 | * 1/1992 | Hooper et al. | 607/19 |
| 5,127,404 | 7/1992 | Wyborny | 607/32 |
| 5,137,019 | * 8/1992 | Pederson et al. | 128/734 |
| 5,143,065 | * 9/1992 | Adkins et al. | 607/19 |
| 5,154,170 | 10/1992 | Bennett | 607/17 |
| 5,271,395 | 12/1993 | Wahlstrand | 607/9 |
| 5,312,441 | 5/1994 | Mader | 607/5 |
| 5,320,643 | 6/1994 | Roline | 607/28 |
| 5,441,524 | 8/1995 | Rueter | 607/18 |
| 5,480,414 | * 1/1996 | Stroebel et al. | 607/28 |
| 5,556,421 | * 9/1996 | Prutchi et al. | 607/36 |

OTHER PUBLICATIONS

Anonymous, Research Disclosure No. 37150, "Use of Heart Sounds as Input to Cardiac Assist Devices" (Mar., 1995).

* cited by examiner

Primary Examiner—Carl H. Layno
(74) Attorney, Agent, or Firm—Michael B. Atlass; Harold R. Patton

(57) ABSTRACT

In a pacemaker, a method and apparatus for providing rate response in proportion to the patient's metabolic demand for cardiac output as determined in response to the patient's breathing rate or respiratory minute ventilation or contraction strength, optionally augmented by the patient's activity level. An implantable pulse generator (IPG) has one or more pacing leads having a proximal end coupled to the IPG and a distal end in contact with a patient's heart. A pressure wave transducer mounted in the IPG in relation to the proximal end of the pacing lead senses pressure waves transmitted from the distal end of the pacing lead to the proximal end thereof. The pressure waves originate from disturbances imparted to the lead by heart contractions and breathing. A further isolated, reference sensor is also incorporated into the IPG in a similar fashion. An activity signal processor is coupled to the pressure wave or reference sensor for providing a patient activity physiologic signal. A respiration signal processor is coupled to said pressure wave and reference transducers for nulling out common mode noise and providing physiologic respiration rate and/or respiratory minute ventilation signals. A contraction strength signal processor is coupled to said pressure wave and reference transducers for nulling out common mode noise and providing physiologic contraction strength signals. Pacing rate control circuitry is responsive to one or more of the physiologic signals for setting the pacing rate to meed the metabolic demand.

15 Claims, 10 Drawing Sheets

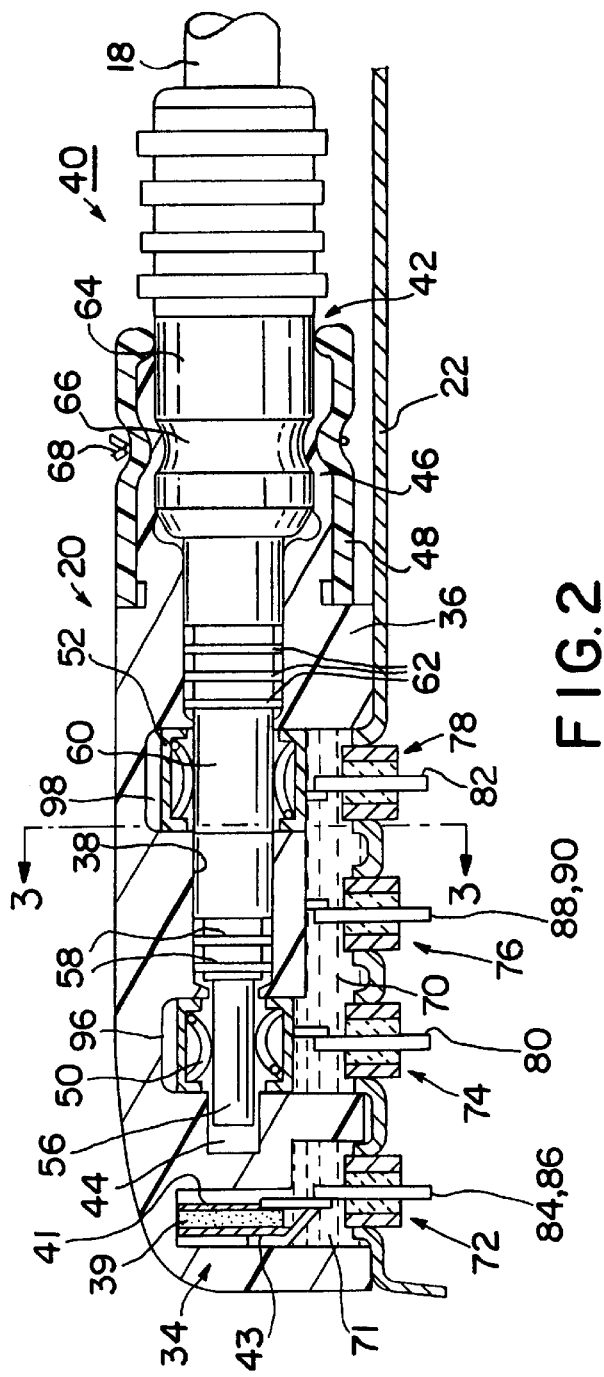
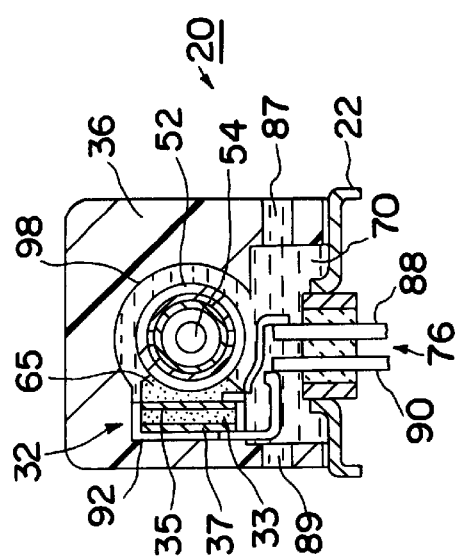
FIG. 2
FIG. 3

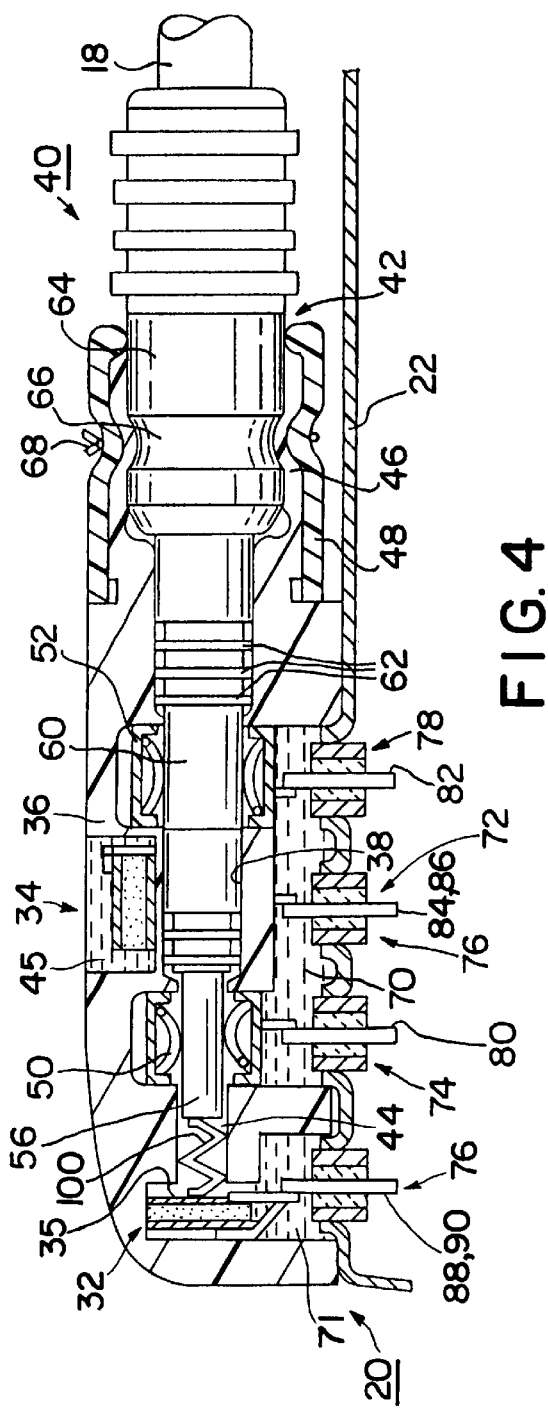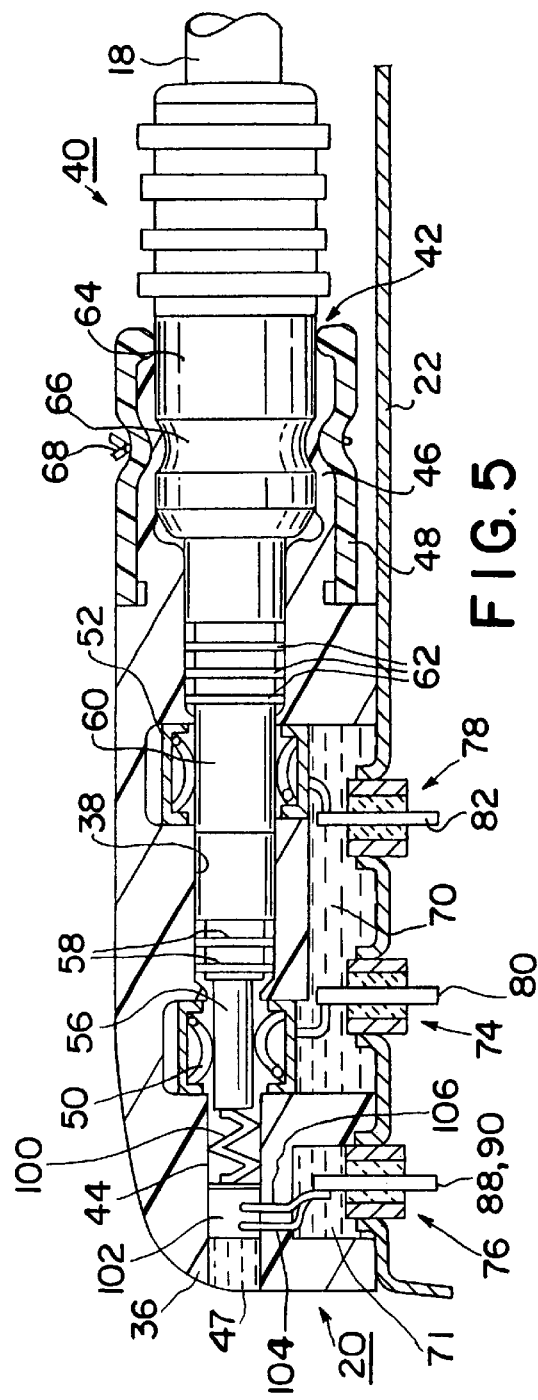

METHOD AND APPARATUS FOR RATE-RESPONSIVE CARDIAC PACING USING HEADER MOUNTED PRESSURE WAVE TRANSDUCER

CROSS-REFERENCE TO RELATED APPLICATION

Reference is hereby made to commonly assigned U.S. patent application Ser. No. 08/623,029 filed on even date herewith and entitled DETECTION OF PRESSURE WAVES TRANSMITTED THROUGH CATHETER/LEAD BODY, and Ser. No. 08/623,443 filed on even date herewith and entitled VERIFICATION OF CAPTURE USING PRESSURE WAVES TRANSMITTED THROUGH A PACING LEAD, and Ser. No. 08/346,813 filed Nov. 30, 1994, for METHOD AND APPARATUS FOR RATE-RESPONSIVE CARDIAC PACING.

FIELD OF THE INVENTION

The present invention generally relates to implantable pacemakers and more particularly to a method and apparatus for providing rate response in proportion to the patient's metabolic demand for cardiac output as determined in response to the patient's breathing rate or respiratory minute ventilation or cardiac contraction strength optionally augmented by the patient's activity level.

BACKGROUND OF THE INVENTION

As described in commonly assigned U.S. Pat. No. 5,320,643 to Roline et al., incorporated herein by reference, a cardiac pacemaker implantable pulse generator (IPG) is an electrical device used to supplant some or all of an abnormal heart's natural pacing function by delivering appropriately timed electrical stimulation signals designed to cause the myocardium of the heart to contract or "beat", i.e. to "capture" the heart. Stimulation pulses provided by implanted pacemakers usually have well-defined amplitude and pulse width characteristics which can be adjusted by remote programming and telemetry equipment to meet physiologic and device power conservation needs of the particular patient.

For state-of-the-art pacemakers, the rate at which stimulation signals are delivered may be variable, and such variation may occur automatically in response to detected changes in a patient's level of physical activity. Such rate-responsive or activity-responsive pacemakers depend on physiologically-based signals, such as signals from sensors which measuring naturally-occurring (intrinsic) cardiac electrical activity, or which measure the pressure inside the patient's ventricle. Such physiologically-based signals provide information regarding cardiac function and the need for pacemaker intervention, and thus are useful for determining a patient's metabolic demand for oxygenated blood.

One popular method for measuring a patient's demand for oxygenated blood is to monitor the patient's level of physical activity by means of a piezoelectric, microphone-like transducer mounted within and against the IPG can. A pacemaker which employs such a method is disclosed in U.S. Pat. No. 4,485,813 to Anderson et al.

In typical prior art rate-responsive pacemakers, the pacing rate is determined according to the output from an activity sensor. The pacing rate is variable between a predetermined maximum and minimum level, which may be selectable by a physician from among a plurality of programmable upper and lower rate limit settings. When the activity sensor output indicates that the patient's activity level has increased, the pacing rate is increased from the programmed lower rate by an incremental amount which is determined as a function of the output of the activity sensor. That is, the rate-responsive or "target" pacing rate in a rate-responsive pacemaker is determined as follows:

$$\text{TargetRate} = \text{ProgrammedLowerRate} + f(\text{SensorOutput})$$

where f is typically a linear or monotonic function of the sensor output.

As long as patient activity continues to be indicated, the pacing rate is periodically increased by incremental amounts until the rate computed according to the above formula is reached (or until the programmed upper rate limit is reached, whichever is lower). In this way, an elevated pacing rate (i.e., one higher than the programmed lower rate limit) may be sustained during periods of patient activity. When patient activity ceases, the pacing rate is gradually reduced, until the programmed lower rate limit is reached.

For any of the known rate-responsive pacemakers, it is clearly desirable that the sensor output correlate to as high a degree as possible with the actual metabolic and physiologic needs of the patient, so that the resulting rate-responsive pacing rate may be adjusted to appropriate levels. A piezoelectric activity sensor can only be used to indirectly determine the metabolic need. The physical activity sensed by a piezoelectric transducer may in some cases be influenced by upper body motion. Therefore, an exercise that involves arm motion may provide signals that are inappropriately greater than the metabolic need. Conversely, exercises that stimulate the lower body only, such as bicycle riding, may provide a low indication of metabolic need while the actual requirement is higher.

To address these perceived disadvantages in the prior art, it has been proposed to utilize other physiologically-based parameters in assessment of a patient's metabolic demand. Respiratory minute ventilation ($V_E$) has been demonstrated clinically to be a parameter that correlates directly to the actual metabolic and physiologic needs of the patient. Respiratory minute ventilation is defined by the equation:

$$V_E = RR \times TV$$

where RR=respiration rate in breaths per minute, and TV=tidal volume in liters. Clinically, the measurement of $V_E$ is performed by having the patient breathe directly into a device that measures the exchange of air and computing the total volume per minute. The direct measurement of $V_E$ is not practical with an implanted device. However, measurement of the impedance changes of the thoracic cavity can be implemented with an implanted pacemaker, and transthoracic cardiac impedance has been shown to correlate well with $V_E$. A pacemaker that is provided with impedance measurement capabilities is disclosed in U.S. Pat. No. 4,702,253 to Nappholz et al. The magnitude of the change of the impedance signal corresponds to the tidal volume and the frequency of change corresponds to respiration rate. Thus, measurement of cardiac impedance can be used as one method for obtaining $V_E$ data.

In practice, cardiac impedance can be measured through assessment of the impedance present between two or more cardiac electrodes, such as the electrodes otherwise used for pacing and/or sensing in connection with a cardiac pacemaker. In particular, it has been shown that cardiac impedance can be measured by delivering constant-current excitation pulses between two "source" electrodes, such that the current is conducted through some region of cardiac tissue.

The voltage differential between two "recording" electrodes can then be measured to ascertain the impedance as reflected by the voltage differential arising from the conduction of the excitation current pulses through the tissue.

In U.S. Pat. No. 4,721,110 to Lampadius, there is described a rheographic arrangement for a cardiac pacemaker in which the base pacing rate of the pacemaker is determined, in part, by a rheographically derived respiration rate signal. Correlation of breathing and intrathoracic pressure fluctuations with impedance of blood in the heart is also recognized in U.S. Pat. No. 4,884,576 to Alt, which describes the measurement of impedance between two electrodes. According to the '576 patent, low-pass filtering of the impedance signal yields a signal from which the patient's respiratory rate can be derived, while high-pass filtering of the same signal yields a signal from which the patient's cardiac function can be observed.

There are currently several commercially available, implantable, rate-responsive IPGs which employ rheographic techniques to adjust the pacing rate in response to metabolic needs. For example, the Biorate IPG manufactured by Biotec International, Bologna, Italy, uses a bipolar rheographic arrangement to monitor the patient's respiration rate. The Meta-MV IPG manufactured by Telectronics, Inc., Englewood, Colo., uses a tripolar rheographic arrangement to monitor the patient's metabolic demand for oxygenated blood. The Precept IPG manufactured by CPI, St. Paul, Minn., uses a tetrapolar rheographic configuration to monitor the patient's pre-ejection interval (PEI), stroke volume, and heart tissue contractility.

The Legend Plus™ IPG, manufactured by Medtronic, Inc., Minneapolis, Minn. and currently undergoing clinical trials in the United States is another example of an implantable pacemaker which employs rheography in support of its rate-response function. The Legend Plus™ IPG delivers a biphasic excitation signal between the pulse generator's canister (serving as an indifferent electrode) and a ring electrode of a transvenous pacing/sensing lead. Impedance sensing in the Legend Plus™ IPG is carried out between the lead's tip electrode and the pulse generator canister. The Legend Plus™ impedance measuring circuitry generates an impedance waveform in which both respiration and cardiac systole are reflected. This waveform is used by the pacemaker's circuitry to derive a minute ventilation value $V_E$, as defined above. The Legend Plus™ IPG periodically assesses a patient's $V_E$, and adjusts its base pacing rate up or down in accordance with the metabolic demand reflected in the $V_E$ value. Various aspects of the Legend Plus™ IPG are described in greater detail in commonly assigned U.S. Pat. No. 5,271,395 to Wahlstrand et al., incorporated by reference herein in its entirety.

Another disclosure which relates to the use of rheography in connection with an implanted device can be found in co-pending U.S. patent application Ser. No. 08/233,901 filed on Apr. 28, 1994, in the name of Wahlstrand et al. entitled METHOD AND APPARATUS FOR SENSING OF CARDIAC FUNCTION, which proposes a method and apparatus for obtaining an impedance waveform. The Wahlstrand et al. application, which relates to the use of a specialized lead for improving the quality of an impedance waveform like that utilized in the aforementioned Legend Plus™ IPG, is hereby incorporated by reference herein in its entirety.

Yet another disclosure relating to the use of rheography in connection with implantable devices can be found in co-pending U.S. patent application Ser. No. 08/277,051 filed on Jul. 19, 1994, in the name of Gianni Plicchi et al., entitled TIME-SHARING MULTI-POLAR RHEOGRAPHY.

As noted above, the utilization of a piezoelectric transducer in a cardiac pacemaker provides a useful but only an indirect indication of a patient's actual level of physical activity, and thus allows for the possibility of false positive or false negative indications of elevated levels of a patient's metabolic demand. The above-noted problem associated with upper body movement is one example of this.

Similarly, the measurement of intracardiac impedance using rheographic techniques provides a useful but somewhat indirect indication of a patient's respiration and cardiac rates, and therefore also allows for the possibility of error in determining a patient's metabolic need. It has been shown that the use of transthoracic impedance to indicate minute ventilation levels has the potential for false positive indications of elevated metabolic demand levels, due to upper body myopotential interference and postural changes. Furthermore, slow-acting physiologic parameters such as transitory blood chemistry changes can also impact impedance measurement.

In addition, basing pacing rate solely on respiratory minute ventilation measurements does not always provide an optimum pacing rate increase at the onset of exercise. Tidal volume (TV) and respiration rate (RR) levels have an inherent physiological time delay due to the response of the $CO_2$ receptors and the autonomic nervous system. An increase in $V_E$ can lag behind the need for increased cardiac output.

On the other hand, activity signals derived from a piezoelectric transducer do not typically exhibit this same time delay phenomenon at the onset of exercise. Moreover, minute ventilation signals derived from transthoracic impedance measurements tend to be more appropriately proportional to a wider variety of types of exercise (e.g., bicycling, walking, running, etc . . . ) than piezoelectric sensor signals tend to be. In this regard, piezoelectric activity signals and transthoracic impedance measurements are mutually complementary in their efficacy in establishing a patient's level of metabolic demand. That is, the potential limitations of each type of sensing are different. This suggests that a combination of activity sensing using a piezoelectric transducer and minute ventilation sensing using rheographic techniques would provide an improved method of accurately tracking a patient's level metabolic demand. Such an approach is set forth in the above-referenced '813 application and in commonly assigned U.S. Pat. No. 5,441,524 to Rueter et al., incorporated by reference herein.

Similarly, the combination of two or more rate control parameters (RCPs), e.g. piezoelectric activity sensors and blood pressure sensors, has also been proposed in commonly assigned U.S. Pat. No. 5,154,170 to Bennett et al., incorporated by reference herein. The '170 patent sets forth an optimization routine for assigning weighting values to the enabled sensor outputs for deriving the appropriate pacing rate in a variety of circumstances.

In virtually all of the approaches, it is necessary to rely on additional components and circuitry, e.g. additional subcutaneous leads or electrodes and/or a current signal generator for making the impedance change measurements which consumes more energy.

In U.S. Pat. No. 4,763,646 to Lekholm, a heart sound detector is also proposed to be mounted in one or more pacing leads arranged in or about the heart or to be mounted in the IPG case for acoustically sensing heart sounds transmitted through a fluid filled lumen. The use of a pressure sensor, microphone or accelerometer is proposed for the heart sound detector.

In one further approach set forth in U.S. Pat. No. 5,063,927 to Webb, the output signal of a piezoelectric activity sensor mounted in the IPG can is filtered to derive an activity signal and a respiration rate signal in lieu of using the rheography technique described above. Respiratory minute ventilation is not described and may be difficult to distinguish from other sources of in-band false signals detected by a piezoelectric activity sensor mounted to the IPG can.

A need exists therefore for a body implantable, durable, long lived, simple and low power sensor for accurately detecting both the respiration rate and tidal volume of the patient for use in determining the physiologic need for cardiac output and automatically adjusting the pacing rate.

SUMMARY OF THE INVENTION

In view of the foregoing considerations, the present invention is directed to an improved method and apparatus for implementing rate-responsive cardiac pacing in a body-implantable pulse generator system.

In particular, the present invention relates to a pacemaker which utilizes a sensor located in the pulse generator in direct or indirect mechanical contact with the pacing lead body for providing a variable amplitude and frequency, physiologic signal from which a rate response signal for adjusting the pacing rate to the need for cardiac output may be derived. In accordance with a preferred embodiment of the invention, the sensor is piezoelectric crystal, pressure wave transducer mounted in the connector block assembly of the IPG in relation to the lead connector end of a pacing lead attached thereto. The pacing lead distal end is in contact with the patient's heart and the elongated lead body traverses a portion of the patient's chest between the heart and the implantation site of the IPG. A pressure wave caused by respiratory expansion and contraction of the patient's chest or contractions of the patient's heart is developed in or transmitted by the lead body to the pressure wave transducer. The pressure wave transducer responds by developing a pressure wave signal of varying amplitude and frequency which reflects both sources.

Preferably, a further piezoelectric, reference transducer is mounted in the connector assembly and isolated from the lead connector end. A reference signal is derived for use in minimizing the effects of common mode noise on the respiration signal. The reference transducer may also be mounted to respond to pressure waves caused by patient activity, principally patient footfalls, transmitted through the patient's body and not necessarily through the lead body.

In a first aspect of the invention, a respiration signal may be derived by respiration sensing circuitry from the pressure wave imparted to the pacing lead during respiration. The patient respiration rate and tidal volume may be derived from the respiration signal, and respiratory minute ventilation may be derived employing the above-described formulas. The present invention thereby provides a variable pacing rate which increases or decreases in response to perceived changes in a patient's physiologic demand as reflected by respiration without the need for impedance signal processing, e.g. rheography. The physiologic demand may be derived from the output signal of the sensor in direct relation to respiration rate or to respiratory minute ventilation and employed to adjust pacing rate.

In a further aspect of the invention, the output signals of the reference transducer and/or the pressure wave transducer may be processed by activity sensing circuitry to derive an activity signal from which a pacing rate adjustment may be made as described above.

In accordance with another aspect of the present invention, the pressure wave and reference wave signals may also be processed to derive a heart contraction signal representative of the intrinsic or evoked contraction of the heart. The strength of contraction of the heart may be related to the autonomic nervous system response to the current need for cardiac output, i.e., the physiologic demand. The heart contraction signal amplitude may be determined in heart contraction sensing circuitry and employed as a contraction strength signal for adjusting the pacing rate.

The rate-response transfer functions may also be based upon a combined or "blended" physiologic demand signal which represents contributions from any two or all three signals of the activity processing circuitry, the respiration rate or respiratory minute ventilation processing circuitry and the heart contraction strength processing circuitry.

The respiration, activity and contraction strength pressure wave processing circuitry can be separately and independently enabled for combination or disabled. If any pressure wave signal processing circuitry is disabled, the rate-response transfer function (i.e., the IPG rate-response behavior) is based solely upon the remaining enabled processing circuitry.

Advantageously, these three physiologic signals (RCPs) related to the metabolic demand for cardiac output may be determined with only one pressure wave transducer mounted in the connector assembly in relation to the lead proximal connector end for detecting pressure waves transmitted through the pacing lead and a reference transducer/activity sensor for detecting pressure waves conducted through the patient's body arising from patient activity. No additional pacing lead conductors are required, and existing physiologic signal processing circuitry and rate setting algorithms and circuitry may be employed in determining a pacing rate to meet the metabolic demand for cardiac output.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 2 is a side cross-section view of a lead connector assembly taken along lines 2—2 of FIG. 1 within which at least a piezoelectric crystal pressure wave transducer and a reference transducer are incorporated in relation to the lead proximal connector end in accordance with a first embodiment of the invention;

FIG. 3 is an end cross-section view taken along lines 2—2 of the connector assembly of FIG. 2;

FIG. 4 is a side cross-section view of a lead connector assembly also taken along lines 2—2 of FIG. 1 within which at least a piezoelectric pressure wave transducer and a reference transducer are incorporated in relation to the lead proximal connector end in accordance with a second embodiment of the invention;

FIG. 5 is a side cross-section view of a lead connector assembly also taken along lines 2—2 of FIG. 1 within which an accelerometer pressure wave transducer is incorporated in in-line relation to the lead proximal connector end in accordance with a third embodiment of the invention;

DETAILED DESCRIPTION OF THE PREFERRED EMBODIMENTS

The preferred embodiment of the invention is illustrated in the context of an implantable single or dual chamber pacemaker IPG of the type described in detail in the above-incorporated '524, '170 and '643 patents or an implantable pacemaker-cardioverter-defibrillator IPG of the type described in commonly assigned U.S. Pat. No. 5,312,441, (having a rate responsive, bradycardia pacing mode) all incorporated herein by reference in their entireties. In such IPGs, the connector assembly is molded as a separate piece part and attached to the hermetically sealed case or can for the power source and electronic components in a manner shown, for example, in commonly assigned U.S. Pat. No. 5,070,605, incorporated herein by reference.

Figure 1:
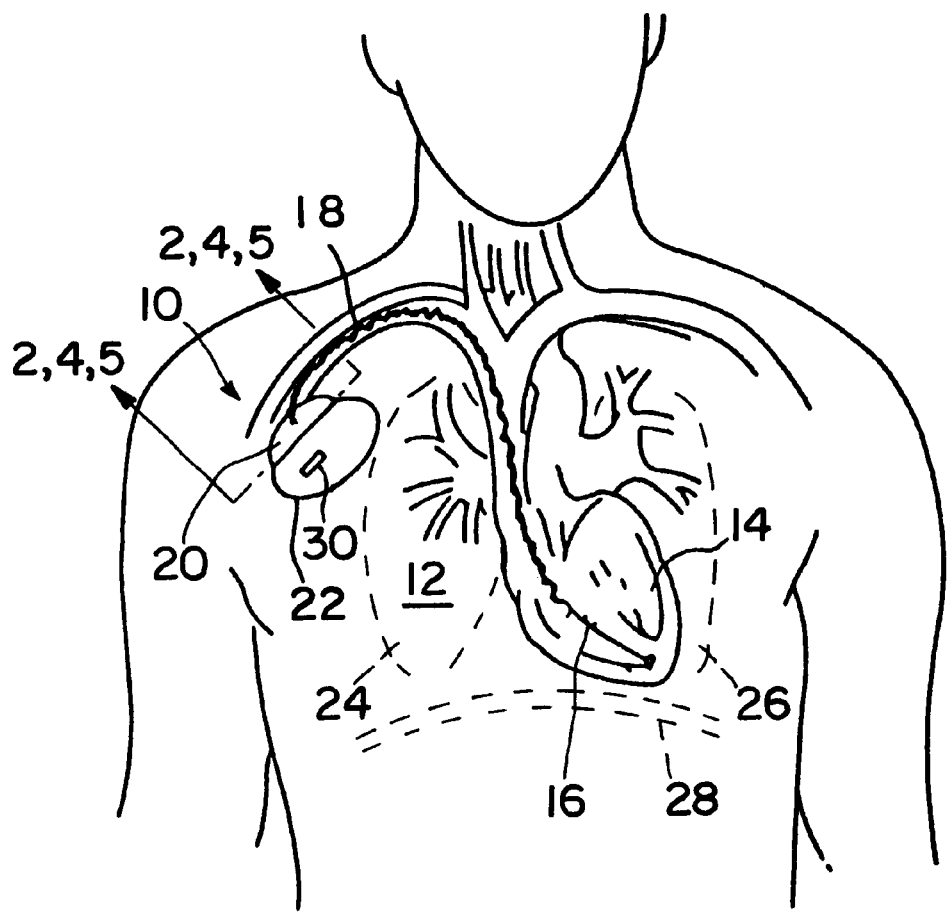
FIG. 1 is a schematic illustration of an IPG implanted in a patient's chest and an endocardial lead transvenously introduced into the heart and traversing the patient's chest.

FIG. 1 is a schematic illustration of such an IPG 10 implanted in a patient's chest 12 and an endocardial lead 18 (or leads) transvenously introduced into the heart 14 and traversing the patient's chest 12. The IPG 10 includes the connector assembly 20 and the case or can 22 enclosing the power supply and circuitry. The combination of the IPG 10 and the lead(s) 18 constitutes a pacemaker.

As the heart 14 contracts and expands, it creates cardiac contraction pressure waves which are transmitted into the distal end segment 16 of lead 18 and are conducted proximally to the relatively still IPG 10. The heart contraction may be intrinsic or it may be evoked by a pacing stimulus.

Similarly, as the lungs 24, 26 expand and contract the pleural cavity and chest with the respiration cycle controlled by the diaphragm 28, the chest movement creates respiratory pressure waves that impart movement to the elongated lead 18 and are conducted proximally to the relatively still IPG 10.

Since the lead distal end segment 16 is typically firmly attached to the heart 14 (and may in fact be alternatively attached to the epicardium) so that good electrical contact is maintained, the cardiac contraction pressure wave may constitute a reaction to a physical shock, i.e. a rapid mechanical movement, imparted to the distal end segment of the relatively forceful contraction of the heart. The transmitted cardiac contraction pressure wave may comprise the mechanical movement itself effecting an acoustic or ringing response of the lead body and may include a component of the actual cardiac contraction sound, and we define it as such.

We have discovered that the cardiac contraction pressure wave, whatever its origin or constituents, may be readily detected and measured at the proximal connector end of the lead 18 by a sensor in direct or indirect mechanical contact with the lead because of its characteristic frequency and amplitude components. Similarly, we have discovered that the respiration pressure wave, which is more gradual and primarily attributable to mechanical motion of the lead body, may also be readily detected at the proximal connector end of the lead 18. These discoveries allows the replacement of sensors in the distal tip segment, which suffer deficiencies detailed in the above-referenced '(P-3810A) and '(P-3810B) applications, with a pressure wave sensor in the IPG (preferably in the connector block) in order to detect and distinguish respiration and/or heart contraction pressure waves. The respiration pressure waves have frequency and amplitude components that may be distinguished from the cardiac contraction pressure waves and other pressure waves impinging on the pressure wave transducer, including patient activity induced body pressure waves.

In this regard, pressure waves that originate elsewhere and are transmitted through the body may also result in pressure wave signals conducted through the lead or conducted directly to the connector assembly 20 and case 22. Due to the nature of the preferred piezoelectric pressure wave transducers described below, we have determined that the patient activity signal can also be distinguished by its characteristic frequency and amplitude components from other pressure wave signals. Alternatively, a separate conventional activity sensing transducer or sensor 30 and/or a reference transducer mounted in connector assembly 20 may be employed in sensing patient activity.

FIGS. 2 and 3 depict the lead connector module or assembly 20 coupled with a proximal connector end 40 of a lead 18 and the incorporation of a pressure wave transducer 32 and a reference transducer 34 in accordance with a first embodiment of the invention. Although a specific connector block and lead type are illustrated in the figures, it will be understood that the invention may be practiced with any lead configuration having in-line or bifurcated lead proximal connector ends and connector assembly configurations for such lead connector ends.

In this first embodiment, the transducers 32 and 34 are each formed of a piezoelectric crystal of the type employed as an activity sensor in commercially available MEDTRONIC® THERA® DR IPGs for rate-responsive pacing in the DDDR mode and other modes. Piezoelectric activity sensor 30 is preferably bonded to the inner surface of the pacemaker's hermetic enclosure or can 22, in accordance with conventional practice in the art. Such an arrangement is disclosed, for example, in commonly assigned U.S. Pat. No. 4,485,813 to Anderson et al., incorporated by reference herein in its entirety.

The pressure wave and reference transducers 32, 34 are formed of a rectangular piezoelectric crystal of about 0.250× 0.125×0.022 inches which is reduced in length and width from the activity sensor 30 to the extent necessary to fit within the connector block assembly 20. The major opposed surfaces of the piezoelectric crystal 33 are coated with thin film electrodes 35 and 37, and the major opposed surfaces of the piezoelectric crystal 39 are coated with thin film electrodes 41 and 43 that are electrically attached to sensor lead wires as described below. The resulting capacitive transducer provides an electrical output signal on the sensor lead wires that varies in amplitude in response to minute deflections of the piezoelectric crystal in response to the mechanically conducted cardiac and respiratory pressure waves as well as body conducted pressure waves emanating from patient activity.

It should be noted that the orientation of the reference transducer 34 should be in a parallel plane with plane of the pressure wave transducer 32, rather than in a transverse plane as depicted for convenience of illustration in the FIGS. 2 and 3. The parallel orientation provides a more exact response of both transducers to common mode noise originating elsewhere in the body, for example.

Figure 6:
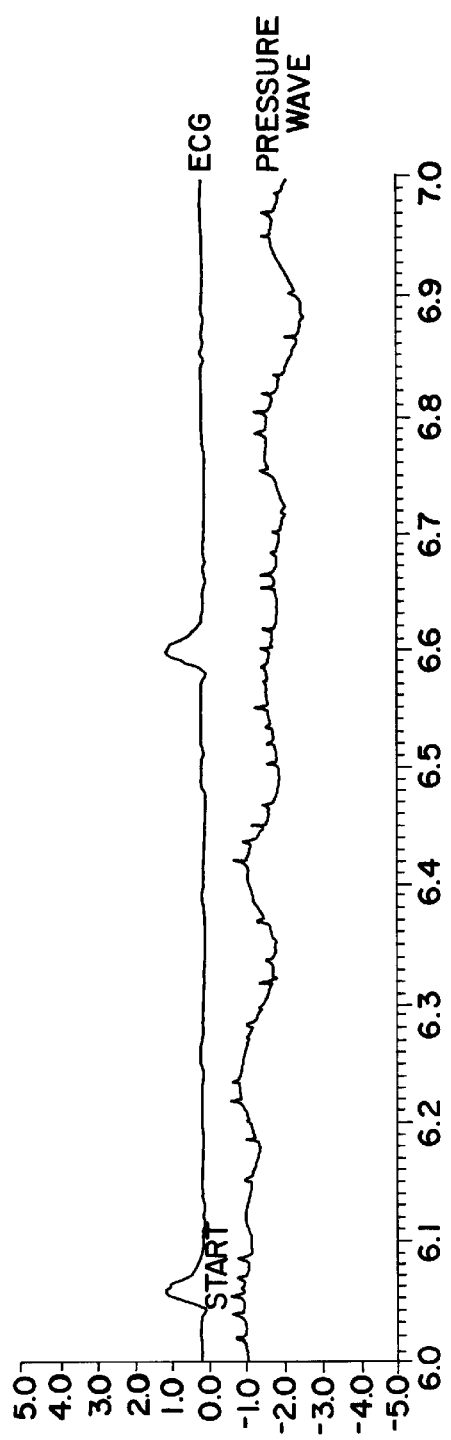
FIG. 6 is a waveform diagram depicting the cardiac cycle pressure waves detected by a single pressure wave transducer in relation to preceding intrinsic PQRST complexes.

The connector assembly 20 shown in FIGS. 2 and 3 is similar to that described and shown in FIGS. 4–6 of the above-incorporated '605 patent. In particular, the connector 20 is formed of a connector housing 36 of uncolored, transparent epoxy molded to form an elongated, lead connector end bore 38 open at the tubular end 42 and terminating in a pin receptacle chamber 44. The connector housing 36 also encloses the transducers 32, 34, feedthrough terminal pins identified below and in-line lead retainers 50 and 52 described below. A flexible sleeve 48 fits over tubular end extension 46.

The bore 38 is shaped to receive the proximal connector end 40 of in-line, bipolar lead 18. The lead 18 is typically constructed of coaxially arranged and electrically insulated coiled wire conductors extending the length of an outer insulating sheath and forming the lead body surrounding a lumen 54 but may be constructed without a lumen. The proximal connector end 40 conforms to the IS-1 standard for bipolar in-line lead connectors and includes a proximal connector pin 56 coupled to the inner coiled wire conductor and sized to fit within the pin engaging, deflectable beam, cylindrical lead retainer 50. An insulating sheath overlies the junction of the connector pin 56 and the inner coiled wire conductor and is formed with annular moisture sealing ribs 58 that engage the walls of the bore 38.

A connector ring 60 is coupled to the outer coiled wire conductor (not shown) and sized to fit within the pin engaging, deflectable beam, lead retainer 52. An insulating sheath overlies the junction of the connector ring 60 and the outer coiled wire conductor and is formed with further annular moisture sealing ribs 62 that engage the walls of the bore 38.

The lead connector end 40 is enlarged to a diameter 64 distally to the connector ring 60 and has an annular groove 66 in diameter 64 shaped to be retained in a necked down annular portion of the tubular end extension 46. The attachment of the lead connector end 40 in the bore 18 may be secured by a suture ring 68. The secure electrical connection of the connector pin 56 with the electrically conductive lead retainer 50 and the connector ring 60 with the electrically conductive lead retainer 52 is described in detail in the above-incorporated '605 patent.

A series of electrical feedthroughs 72, 74, 76, 78 are mounted to extend through the mating surface of the can 22 and into cavities 70 or 71 (preferably minimized into channels) sealed with medical grade silicone rubber adhesive or the like when the connector assembly 20 is attached to the can 22. Lead feedthrough pins 80 and 82 extend through the lead feedthroughs 74 and 78, respectively and are electrically connected to the lead retainers 50 and 52, respectively, by short wire conductors. Reference feedthrough pins 84 and 86 extend through double pin, reference feedthrough 72 and are electrically connected with the thin film electrodes 41 and 43, respectively, of the reference transducer 34 by short transducer wire conductors. Similarly, pressure wave feedthrough pins 88 and 90 extend through double pin, pressure wave feedthrough 76 and are electrically connected with the thin film electrodes 35 and 37, respectively, of pressure wave transducer 32 by short transducer wire conductors. Double pin transducer feedthroughs 72 and 76 may be employed because of the extremely low voltage and current signals generated by the pressure and reference wave transducers 32 and 34.

The connector assembly may be fabricated in one way by positioning the pressure and reference wave transducers 32, 34 and attached wires within opening 92 of cavity 70 and within cavity 71, respectively, and positioning the lead retainers 50 and 52 and attaching wires in the depicted enlarged open portions 96 and 98 of bore 38. The inserted components can then be fixed and sealed from the environment in those positions with silicone rubber adhesive while leaving the ends of the wires exposed for attachment to feedthrough pins. The backfilling of the gap between the pressure wave transducer 32 and the outer surface of the retainer 52 with silicone adhesive ensures that a direct mechanical contact is made with the lead retainer 52 and indirect contact is made with the lead body. Care must be taken to avoid entraining air bubbles in the backfilled silicone rubber adhesive insulating layer between the lead retainer 52 side wall and the adjacent conductive thin film electrode 35.

Alternatively as shown in FIG. 3, the pressure wave transducer 32 is carefully spaced from the lead retainer 52 by an electrical insulating layer 35 to prevent it from contacting the thin film electrode 35 while ensuring indirect contact through the lead retainer 52 to the lead body. In practice, the insulating layer 35 may be a more rigid plastic adhesive for adhering the lead retainer 52 and pressure wave transducer 32 (and associated sensor and retainer leads) together as a sub-assembly that is inserted into the open portion 98 before it is backfilled.

A further alternative approach providing direct contact of the lead retainer 52 with the piezoelectric crystal 33 can be practiced if the two electrodes are deposited on the side where electrode 37 is depicted. Intimate direct contact between the pressure wave transducer 32 and the lead retainer 52 can also be achieved by a thin layer of adhesive at the contact line.

In any case, the connector housing 36 may be formed with welding access ports through which a welding probe may be introduced to weld the conductor wire ends to the feedthrough pins as exemplified by welding ports 87 and 89 shown in FIG. 3. In this final assembly process, the connector assembly 20 is secured to the mating surface of can 22, and the conductor wire ends are welded to the feedthrough pins through the welding access ports. Then, the interior spaces 70, 71 (or channels) and the access ports are backfilled with medical grade silicone rubber adhesive.

The resulting connector assembly 20 of the first embodiment therefore includes a pressure wave transducer 32 that makes direct mechanical contact with the lead 18 and an reference transducer that is isolated from the lead 18 but subjected to common mode noise sources at the location of the IPG 10. For example, such common mode noise sources may include pressure waves induced by body or limb movement, speech, coughing, snoring, footfalls and extraneous ambient noise.

Turning to FIG. 4, it depicts an alternative arrangement of the locations of the piezoelectric crystal pressure wave transducer 32 and reference transducer 34. This orientation allows the direct conduction of mechanical pressure wave energy in the pressure wave conveyed up the lead lumen 54 to deflect the piezoelectric crystal 33. The pressure wave transducer 32 is in direct axial alignment with the lead connector pin and mechanically coupled to it by a flexible spacer, e.g. leaf spring 100. The leaf spring 100 is maintained in the end of the bore chamber 44 so that mechanical contact with the lead connector pin 56 may be maintained given lead and connector fit tolerances. As shown, the chamber 44 is extended to the thin film electrode 35, and the non-conductive leaf spring 100 fits in that space. A conductive leaf spring 100 may be used if the thin film electrode 35 is insulated or if the electrode 33 is located alongside electrode 35. All other aspects of the fabrication of the connector assembly 20 of FIG. 4 are similar to those described above.

The reference transducer 34 is located in a cavity 45 in molded housing 36 that is separated from the lead bore 38 by an internal wall of molded housing 36. Channels are also formed in the molded housing 36 to direct the transducer conductors to the reference feedthrough pins 84, 86. After the reference transducer 34 is positioned in the cavity 45, it is backfilled with silicone rubber adhesive. The preferred location for the reference transducer 34 and the related components may vary from that shown in FIG. 4.

In these embodiments of FIGS. 1–4, the placement of the reference transducer 34 and the related conductors and feedthrough 72 is arbitrarily depicted. They may be situated in the connector housing 36 at any convenient location that provides isolation from the pressure wave conducted up the lead 18. The preferred location and orientation of the reference transducer 34 and its related components is in a parallel plane to the plane of the pressure wave transducer 32. In an alternative embodiment, it is possible to eliminate the reference transducer 34 and associated components and employ the signals provided by the activity sensor 30 as reference signals for eliminating common mode noise.

The pressure wave transducer 32 may also be placed at any convenient angle to either of the lead retainers 50 and 52. Moreover, although a single channel IPG 10 is depicted for the sake of simplicity in the preceding drawings, it will be understood that the same approaches may be taken to provide a second pressure wave transducer in relation to a second lead for a dual chamber monitor or IPG of the types incorporated above and described below.

In addition, although piezoelectric crystal transducers of the type described are preferred due to their low cost, reliability, low current drain and responsiveness to pressure waves of the type described, piezoelectric crystal moving beam accelerometers may also be used. Other solid state, micro-miniaturized IC accelerometers and transducers may be substituted for the piezoelectric crystal transducers, including miniature IC beam accelerometers and capacitive accelerometers.

Turning now to FIG. 5, it depicts a further embodiment of the invention employing a micro-miniaturized, accelerometer 102 mounted in alignment with the lead connector pin 56 and in indirect contact therewith through a leaf spring 100. Such accelerometers are typically mounted on a diaphragm, and motion of the diaphragm effects motion of the moving element of the accelerometer.

The accelerometer 102 is inserted into the chamber 44 through an access port 47 in molded housing 36 that is backfilled with silicone rubber adhesive. The accelerometer leads 104, 106 are routed to pressure wave feedthrough pins 88, 90 of the pressure wave feedthrough 76. A reference accelerometer isolated from the pressure wave sensing accelerometer may also be provided in the embodiment of FIG. 5 in the same manner as the reference transducer 34 of FIGS. 2–4. All other aspects of the fabrication of the connector assembly 20 of FIG. 5 and its attachment to the can 22 are similar to those described above.

FIG. 6 is a two second waveform diagram depicting the cardiac cycle pressure wave in relation to the preceding intrinsic PQRST complex. The pressure wave is transmitted up a conventional pacing lead implanted in the ventricle of a healthy dog and detected by a pressure wave transducer in the connector assembly 20. In this experiment, a wide bandpass filter was employed, and only the pressure wave transducer of the embodiment of FIGS. 2 and 3 was used.

A lag between the peaks of the PQRST complex and the peaks of the double pulses is observed that is greater than the lag observed between the PQRST peaks and the peaks of the lub-dub sound waves observed using conventional chest electrodes and sound transducers as described anonymously in *RESEARCH DISCLOSURE* No. 37150, entitled "Use of Heart Valve Sounds as Input to Cardiac Assist Devices" (March, 1995). The double peaks of FIG. 6 may represent the pressure waveform of the ventricles in forcefully contracting and expelling blood and then relaxing and filling with blood that takes place in closer timed relation to the PQRST complex. A clear correlation between the double signal peaks of the pressure wave and the PQRST complex is observed. This correlation is effective with either an intrinsic depolarization or an evoked depolarization of the heart and in both the atrial and ventricular heart chambers.

Figure 7:
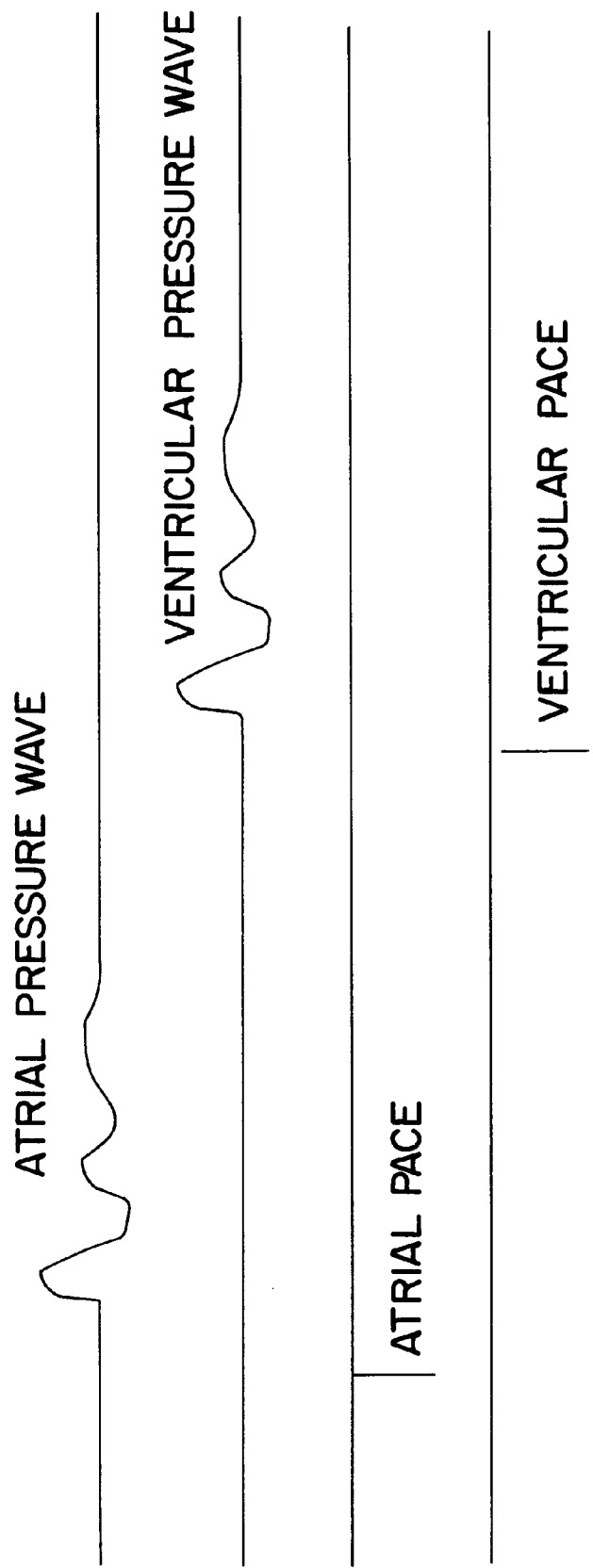
FIG. 7 is a waveform diagram depicting the cardiac cycle pressure waves detected by the atrial and ventricular pressure wave transducers in relation to preceding atrial and ventricular pacing pulses.

FIG. 7 is a waveform diagram depicting the cardiac cycle pressure waves detected by the atrial and ventricular pressure wave transducers in relation to preceding atrial and ventricular pace pulses. In each case, the pace pulse energy is sufficient to capture the atrium and the ventricle as indicated by the double pulse response of the atrial and ventricular pressure transducers located in the connector assembly 20.

The frequency and amplitude components of the double pulse, cardiac contraction, pressure wave signal in response to an intrinsic depolarization shown in FIG. 6 and an evoked depolarization shown in FIG. 7 may be measured and employed as an indicia of the strength of contraction of the heart, in a manner analogous to the use of blood pressure measured within a heart chamber. The frequency range of interest of the cardiac contraction pressure wave is believed to be between about 0.5–7.0 Hz in the atrium and in the ventricle. The strength of the ventricular or the atrial contraction is correlated to the metabolic need or demand for cardiac output as determined by the autonomic nervous system. One or both of the pressure wave signal is processed into a physiologic, contraction strength (CS) signal(s) that may be used alone or in conjunction with the other physiologic signals as described below to adjust the pacing rate to meet the metabolic need.

Figure 8:
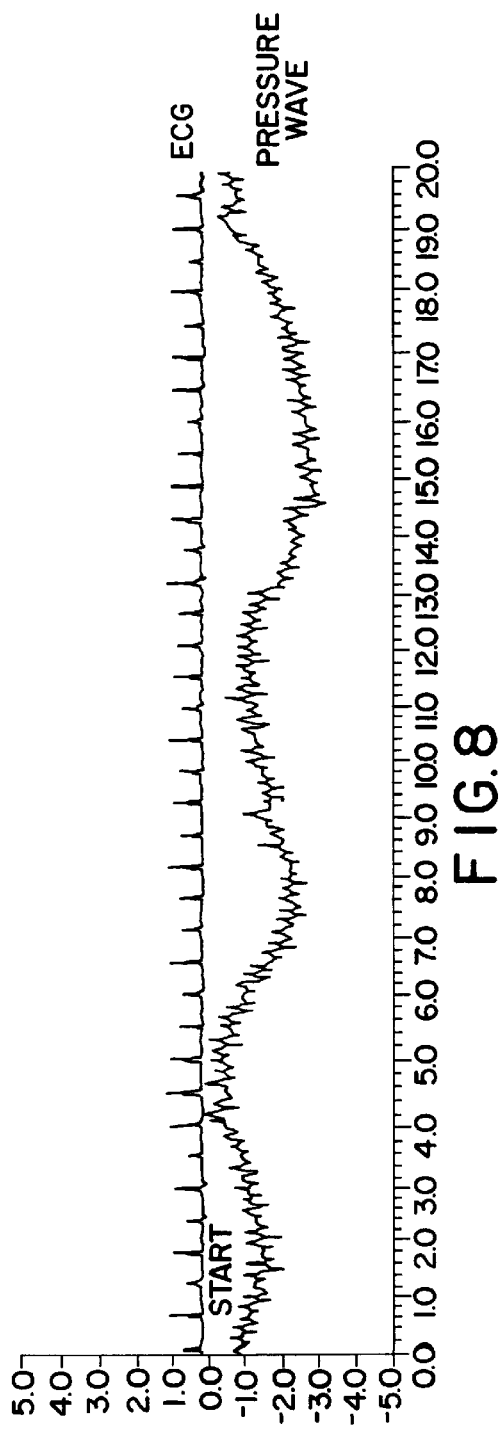
FIG. 8 is a waveform diagram depicting the respiration cycle pressure wave detected by a single pressure wave transducer in relation to a series of intrinsic PQRST complexes.

FIG. 8 is a 20 second waveform diagram depicting the respiration cycle pressure wave detected by the pressure wave transducer in relation to a series of PQRST complexes in the same dog experiment. The respiration cycle is much longer than the cardiac cycle. Because the respiratory cycle alters the baseline amplitude of the pressure wave, the varying baseline signal may be derived and used to adjust the baseline for measurement of the amplitudes of the double pulse, cardiac contraction, pressure wave signals.

The respiration pressure wave therefore has differing frequency and amplitude components from those of the double pulse, cardiac contraction, pressure wave signal. The frequency range of the respiration pressure wave is in the range of about 0.05–0.8 Hz. In accordance with a further aspect of the invention, both respiration rate RR and tidal volume TV may be derived from the waveform of FIG. 8. Consequently, a physiologic signal may be derived for adjusting the pacing rate either in accordance with RR or in accordance with respiratory minute ventilation $V_E$ derived from RR and TV as set forth above.

Finally, although not specifically shown in FIGS. 6–8, the activity signal may be generated on any one or all of the piezoelectric or accelerometer type pressure wave transducers employed in a given IPG, including the separate activity sensor 30, the reference transducer 34 and the active, pressure wave transducer 32 shown in FIGS. 1–4. Patient, activity, particularly footfalls can be distinguished from the pressure waves of FIGS. 6–8, because they have a frequency range between about 0.5–15 Hz and through the use of reference transducers and signal processing, if necessary.

Figure 9:
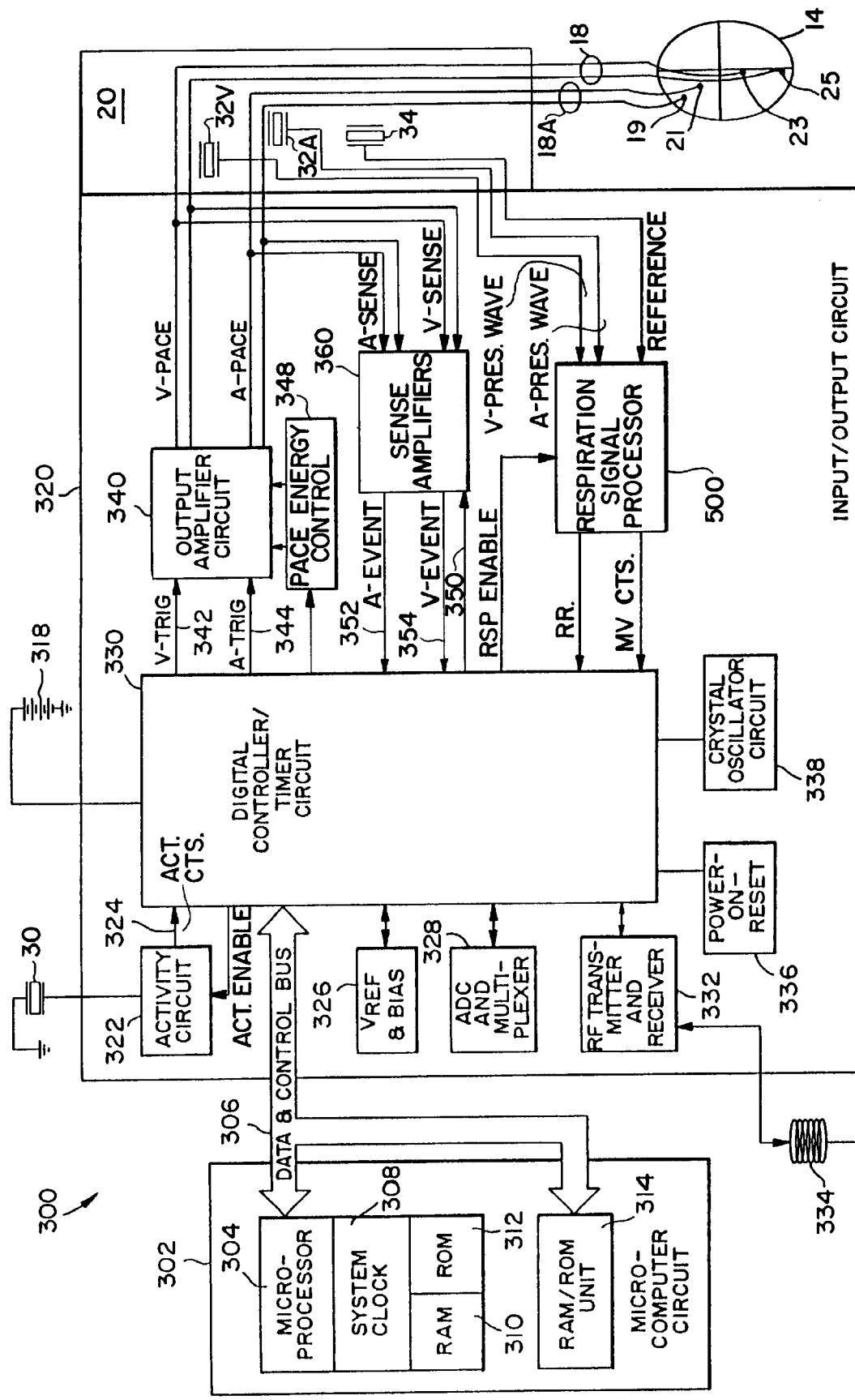
FIG. 9 is a block diagram of a first dual chamber pacemaker embodiment in which the invention is preferably implemented for providing rate-responsive pacing as a function of physiologic signals derived from one or more respiration pressure wave and reference transducers and/or activity sensors.
Figure 11:
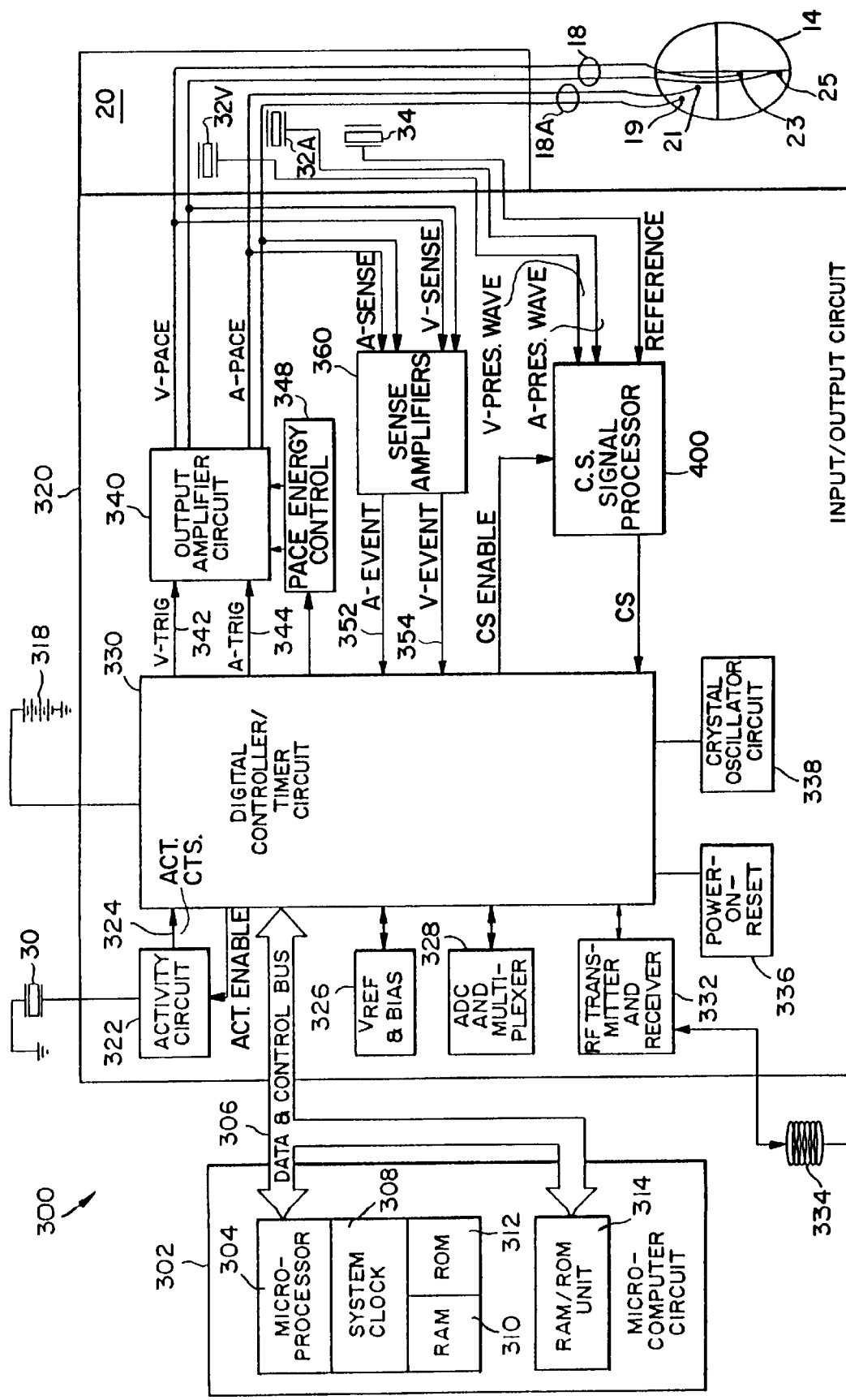
FIG. 11 is a block diagram of a second dual chamber pacemaker embodiment in which the invention is preferably implemented for providing rate-responsive pacing as a function of physiologic signals derived from one or more contraction strength pressure wave and reference transducers and/or activity sensors.
Figure 13:
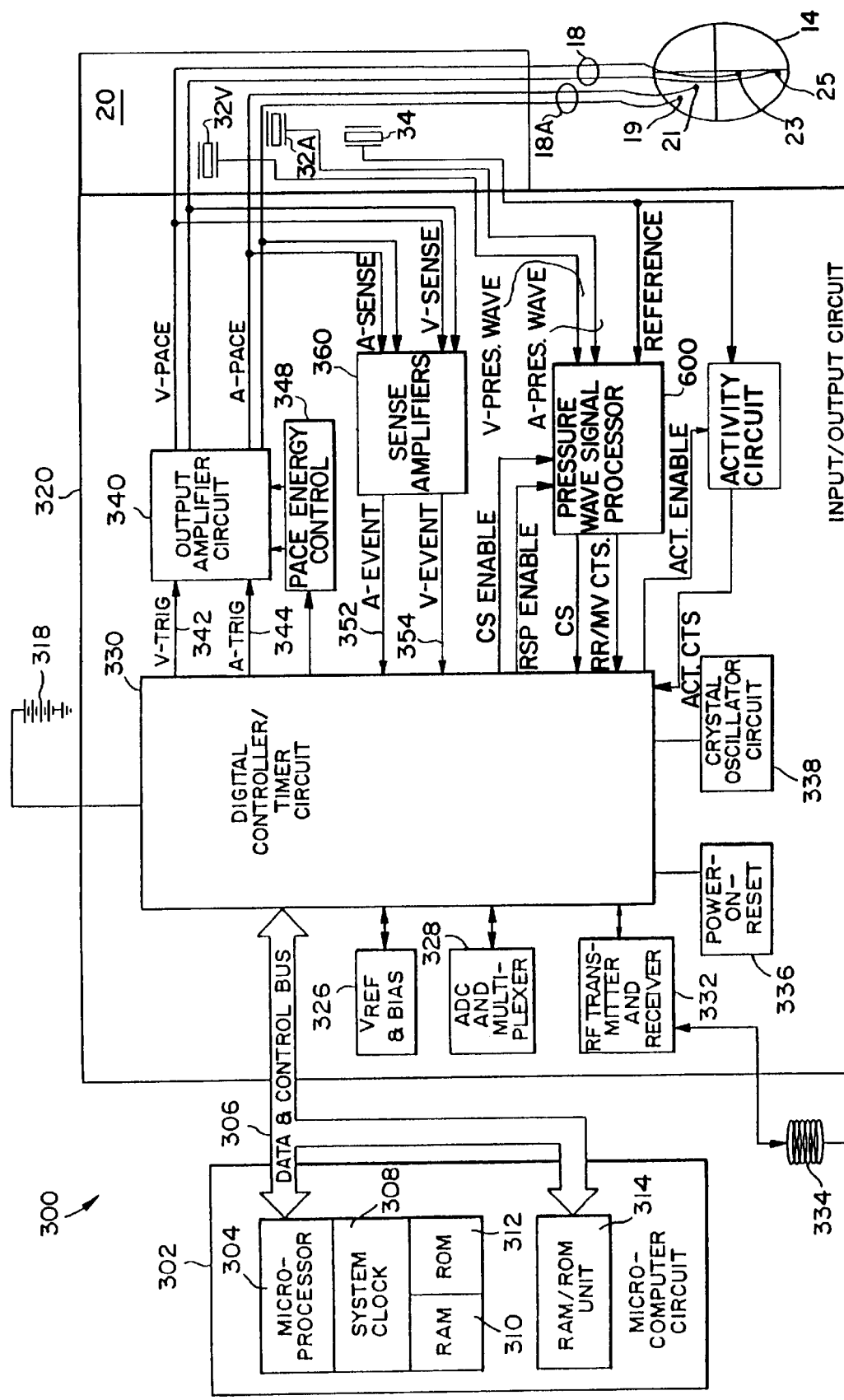
FIG. 13 is a block diagram of a third dual chamber pacemaker embodiment in which the invention is preferably implemented for providing rate-responsive pacing as a function of one or more of the respiration rate, respiratory minute ventilation, patient activity and contraction strength physiologic signals derived in accordance with the circuitry of FIGS. 10 and 12.

Turning now to FIGS. 9, 11, and 13, they depict block diagrams of an IPG circuit 300 of an exemplary dual chamber, rate-responsive IPG 10 and set of atrial and ventricular pacing leads 18A and 18V in which the present invention may be practiced. FIGS. 9, 11, and 13 are intended to be inclusive of single chamber, rate responsive pacemakers in which only a single lead 18A or 18V is present in which the various aspects and embodiments of the present invention may be incorporated. FIGS. 9, 11, and 13 consequently also show both atrial and ventricular pressure wave transducers 32A and 32V, which is intended to be inclusive of the use of only a single such transducer in any given dual or single chamber IPG architecture.

In the embodiment illustrated in FIG. 9, the IPG 10 is provided with a piezoelectric crystal activity sensor 30 which is intended to provide a patient activity physiologic signal particularly in the case where the active transducer(s) 32A and/or 32V is an accelerometer of the type shown in FIG. 5. Alternatively, the activity sensor 30 may be of the same type and characteristics as the piezoelectric or accelerometer pressure wave transducer 32A and/or 32V and may be used in substitution for the reference transducer 34. However, for purposes of illustrating all possible alternatives, a separate reference transducer 34 is also depicted in FIG. 9.

Activity sensor 30 (or reference transducer 34) generates electrical pressure wave signals in response to sensed physical activity (patient footfalls) which are processed by activity circuit 322 in input/output circuit 320 to provide activity signal 324 to digital controller/timer circuit 330. Activity circuit 322 and associated activity sensor 30 may correspond to the circuit and sensor disclosed in U.S. Patent No. 5,052,388 to Sivula et al., incorporated herein by reference in its entirety, and is described further below.

First, the common IPG operating components of FIGS. 9, 11 and 13 are described as follows. Lead 18A is an atrial bipolar pacing lead, carrying two electrodes 19 and 21 positioned in the right atrium of heart 14. Electrodes 19 and 21 are used both to sense and pace the atrium in a manner well known in the art. Similarly, lead 18V represents a ventricular bipolar pacing lead, carrying two electrodes 23 and 25 implanted in the right ventricle of the heart 14. As discussed above in conjunction with atrial lead 18A, electrodes 23 and 25 are used to sense and pace the ventricle in a manner well known in the art.

The IPG circuit 300 located within can 22 includes circuitry performing all of the basic timing, stimulation and sensing functions of a DDD or DDDR cardiac pacemaker. The IPG circuit 300 includes input/output circuit 320, a microcomputer circuit 302, which controls the timing intervals provided by the input/output circuit 320, a battery 318, an activity sensor 30, a telemetry antenna 334, and feedthroughs (not shown) to the lead connector elements in connector block 20, as described above, for making electrical connection with the connector pin and ring, in the case of bipolar leads.

Crystal oscillator circuit 338 within input/output circuit 320 provides the basic timing clock for the components of the IPG circuit 300 through digital controller/timer circuit 330. Battery 318 provides power for all the components of IPG circuit 300. Power-on-reset circuit 336 within input/output circuit 320 responds to initial connection of the circuit to the battery 318 for defining an initial operating condition and also resets the operative state of the device in response to detection of a low battery voltage condition. Reference mode circuit 326 within input/output circuit 320 generates stable voltage references and currents for the analog circuits within the pacing circuit 320. Analog to digital converter ADC and multiplexor circuit 328 within input/output circuit 320 digitizes analog signals and voltage to provide real time telemetry of cardiac signals from sense amplifiers 360 for uplink transmission via RF transmitter and receiver circuit 332. Voltage reference and bias circuit 326, ADC and multiplexor 328, power-on-reset circuit 336 and crystal oscillator circuit 338 may correspond to any of those presently used in current marketed implantable cardiac pacemakers.

Data transmission to and from the external programmer (not shown) is accomplished by means of the telemetry antenna 334 and an associated RF transmitter and receiver 332 within input/output circuit 320, which serves both to demodulate received downlink telemetry and to transmit uplink telemetry. For example, circuitry for demodulating and decoding downlink telemetry may correspond to that disclosed in U.S. Pat. No. 4,556,063, while uplink telemetry functions may be provided according to U.S. Patent Nos. 5,127,404 and 4,374,382. Uplink telemetry capabilities will typically include the ability to transmit stored digital information as well as real time or stored EGMs of atrial and/or ventricular electrical activity (according to the teaching of the above-cited '404 patent), as well as transmission of Marker Channel pulses indicating the occurrence of sensed and paced depolarizations in the atrium and ventricle, as disclosed in the cited '382 patent.

In addition, in the context of the present invention, data relating to the determination of the physiologic signals and the pacing rate history of the patient may be stored in the RAM 310 or the RAM/ROM unit 314 of microcomputer 302 for later telemetry out on command of the external programmer. This data may be encoded in digital form and transmitted via RF transmitter 332 and antenna 334 to the external programmer 40 for display and/or analysis.

The connector block assembly 20 is also illustrated schematically in FIGS. 9, 11 and 13 in relation to the IPG circuit 300. The bipolar leads 18A and 18V are illustrated schematically coupled directly through the connector block assembly 20 and into the input/output circuit 320. The atrial and ventricular pressure wave sensors 32A and 32V, respectively, are shown schematically in proximity to the proximal connector ends of atrial and ventricular leads 18A and 18V. The reference transducer 34 is shown schematically within the connector block assembly 20. The associated terminals, lead wires and feedthroughs are not shown in FIGS. 9, 11 and 13. In the actual implantable device, connector block 20 and these components for both the atrial and ventricular leads would, of course, take one of the forms described in reference to FIGS. 1–5 and equivalents thereto.

A pace output amplifier circuit 340 in input/output circuit 320 includes a ventricular pulse generator circuit coupled to the ventricle of the heart 14 by means of electrodes 23, 25 on lead 18V as well as an atrial pulse generator circuit coupled to the atrium of heart 14 by means of atrial electrodes 19, 21, located on lead 18A. In order to trigger generation of a ventricular pacing or V-PACE pulse, digital controller/timer circuit 330 generates a trigger signal on V-TRIG line 342. Similarly, in order to trigger an atrial pacing or A-PACE pulse, digital controller/timer circuit 330 generates a trigger pulse on A-TRIG line 344. The A-PACE and V-PACE pulse energies may be controlled in either or both pulse width and pulse amplitude by pace energy control 348 which receives a pace energy command signal from digital timer/controller circuit 330 prior to the delivery of each A-TRIG and V-TRIG signal. In accordance with the present invention, the atrial and ventricular pace pulse energies are determined in response to the determination of the atrial and ventricular pacing thresholds as described below.

Sense amplifier circuit 360 includes atrial and ventricular sense amplifiers coupled to the atrium and ventricle by means of leads 18A and 18V, respectively. The output circuit 340 and sense amplifier circuit 360 may contain pulse generators and sense amplifiers corresponding to any of those presently employed in commercially marketed cardiac pacemakers. Sensed atrial depolarizations or P-waves that are confirmed by the atrial sense amplifier (A-EVENT) in response to an are communicated to the digital controller/timer circuit 330 on A-EVENT line 352. Similarly, ventricular depolarizations or R-waves that are confirmed by the ventricular sense amplifier (V-EVENT) in response to a V-SENSE are communicated to the digital controller/timer circuit 330 on V-EVENT line 354.

Control of timing and other functions within the input/output circuit 320 is provided by digital controller/timer circuit 330, which includes a set of timers and associated logic. Digital controller/timer circuit 330 defines the basic pacing or escape interval, which may take the form of an A—A escape interval initiated on atrial sensing (A-EVENT) or pacing (A-PACE) and triggering atrial pacing (A-PACE) at the expiration thereof or may take the form of a V—V escape interval, initiated on ventricular sensing (V-EVENT) or pacing (V-PACE) and triggering ventricular pulse pacing (V-PACE) at the expiration thereof. Digital controller/timer circuit 330 similarly defines the A-V delay intervals SAV and PAV that commence following a sensed A-EVENT and a delivered A-PACE, respectively. The specific values of the intervals defined are controlled by the microcomputer circuit 302 by means of data and control bus 306 from programmed in parameter values and operating modes.

Digital controller/timer circuit 330 also defines time intervals for controlling operation of the atrial and ventricular sense amplifiers in sense amplifier circuit 360. Typically, digital controller/timer circuit 330 defines an atrial blanking interval following delivery of an A-PACE pulse, during which atrial sensing is disabled, as well as ventricular blanking intervals following atrial and ventricular pacing pulse delivery, during which ventricular sensing is disabled. Digital controller/timer circuit 330 also defines an atrial refractory period (ARP) during which atrial sensing is disabled or the A-EVENT is ignored for the purpose of resetting the escape interval. The ARP extends from the beginning of the SAV or PAV interval following either an A-EVENT or an A-TRIG and until a predetermined time following sensing of a ventricular depolarization or triggering the delivery of a V-PACE pulse. Digital controller/timer circuit 330 similarly defines a ventricular refractory period (VRP), which is typically shorter than the portion of the ARP following ventricular sensing or pacing, following either a V-EVENT or V-TRIG.

In the case of an ectopic V-EVENT, both a VRP and a post-ventricular atrial refractory period (PVARP) defined by the digital controller/timer circuit 330 separately from the ARP may be generated. The durations of the ARP, PVARP and VRP may also be selected as a programmable parameter stored in the microcomputer 302. Digital controller/timer circuit 330 also controls sensitivity settings of the sense amplifiers 360 by means of sensitivity control 350.

Microcomputer 302 controls the operational functions of digital controller/timer circuit 330, specifying which timing intervals are employed, and controlling the duration of the various timing intervals, via data and control bus 306. Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 is interrupt driven, operating in a reduced power consumption mode normally, and awakened in response to defined interrupt events, which may include the A-TRIG, V-TRIG, A-EVENT and V-EVENT signals.

In operation, depending on the programmed RCPs and the pacing rate control mode, the microprocessor 304 defines a pacing rate between a programmed lower rate and an upper rate in dependence on a rate setting circuit within digital controller/timer 330 that responds to one, two or all of the ACTIVITY COUNT signal, the RR COUNT signal or MV COUNT signal, and the contraction strength (CS) signal as described below. The microprocessor 304 also define variable A-V intervals and variable ARPs and VRPs which vary with the escape interval established in response to the selected RCPs. For example, the microprocessor 304 may specify a variable rate adaptive decrement interval (RAD) to be subtracted from the defined A-V delay intervals when the paced (or sensed) heart rate is above the lower rate. Similarly microprocessor 304 may define ARPs and/or VRPs which decrease in duration in relation to an increase in paced (or sensed) heart rate above the lower rate.

The A—A interval is started, and during the A-V delay interval the device awaits either time out of the current A-V delay interval (PAV or SAV) or a V-EVENT. If a V-EVENT does not occur prior to A-V delay interval time out, a V-TRIG is generated at the end of the A-V interval, and the values of the A-V intervals are updated, if necessary. If a V-EVENT is sensed prior to expiration of the current A-V delay interval, the pacemaker's timing may be reset to deliver an A-TRIG at the expiration of a V-A escape interval or at the expiration of the A—A escape interval. If the A—A (or V-A) escape interval expires without any intervening A-EVENT or V-EVENT, an A-PACE pulse is again generated, and the next succeeding A-V delay interval is defined to be equal to a PAV. In the event that a V-EVENT is sensed at prior to expiration of the A—A escape interval, the timing is reset to trigger A-PACE at the expiration of the V-A interval (A—A escape interval minus PAV). If an A-EVENT is sensed prior to expiration of the A—A (or V-A) interval, the subsequent A-V interval is defined to be equal to SAV and the A—A escape and A-V delay intervals are reset. The time interval values, including the A—A escape interval, the SAV and PAV delay intervals, the ARP, VRP and any other time intervals defined by operating algorithms at any particular time are stored in either ROM or RAM and are fetched, used and updated as described above.

As previously noted, the IPG 300 in accordance with the presently disclosed embodiments of the invention may be programmed to operate in several rate-responsive modes in response to a selected one, any two, or all of the physiologic signals or RCPs derived from the pressure wave signals. These physiologic signals may be characterized as an activity RCP signal, a minute ventilation or respiration rate RCP signal, and a cardiac contraction strength RCP signal, in accordance with the nomenclature of the above-incorporated '170 patent. At least the activity RCP signal and the MV RCP signal may be combined in the manner described in the above-incorporated '813 patent application, the '170 patent or the '524 patent. At least the activity RCP signal and the contraction strength RCP signal may be combined in the manner described in the above-incorporated '170 patent.

Turning first to the derivation of the activity RCP signal, it is preferably derived from the activity sensor 30 of FIG. 9 or the reference transducer 34 (as shown in FIG. 13 and which may be one and the same as the activity sensor 30), although it may also be derived from one of the pressure wave transducers 32A or 32V, whichever is present in the IPG architecture.

In any case, the separate activity sensor 30 or the transducer 32/34 is responsive to body pressure waves caused by the activity of the patient and transmitted through the body causing lead body motion. The sensor or transducer provides a pressure wave signal having activity frequency and amplitude components representative of patient activity, specifically footfalls. Pressure wave signal processing means in activity circuit 322 provide an activity count signal "ACT. CTS." in response to the activity frequency and amplitude components of the pressure wave signal as the physiologic signal.

Figure 10:
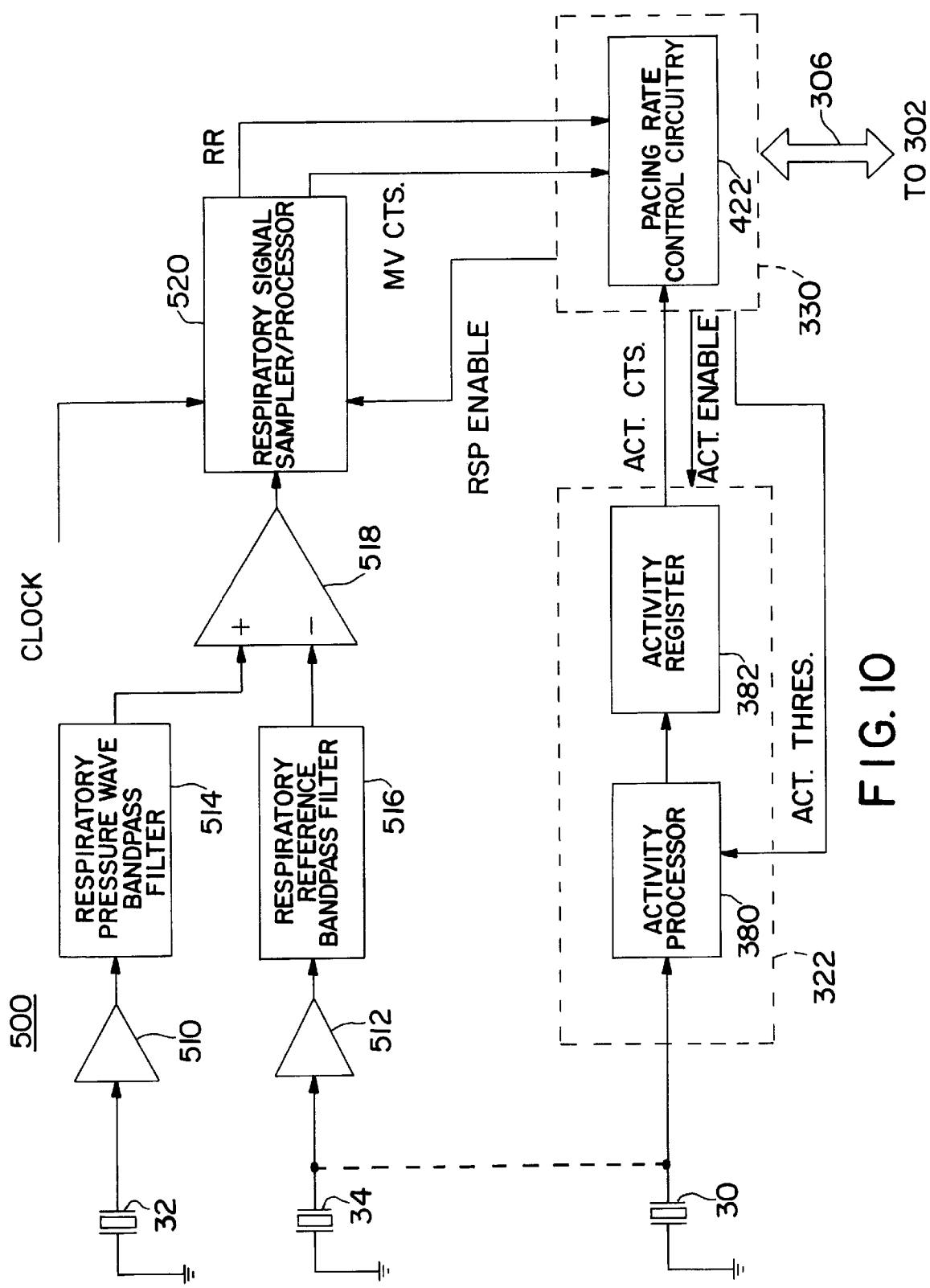
FIG. 10 is a block diagram of signal processing circuitry usable in the system of FIG. 9 for deriving a respiration rate and respiratory minute ventilation physiologic signal and (optionally) an activity count physiologic signal related to the metabolic demand for cardiac output.
Figure 12:
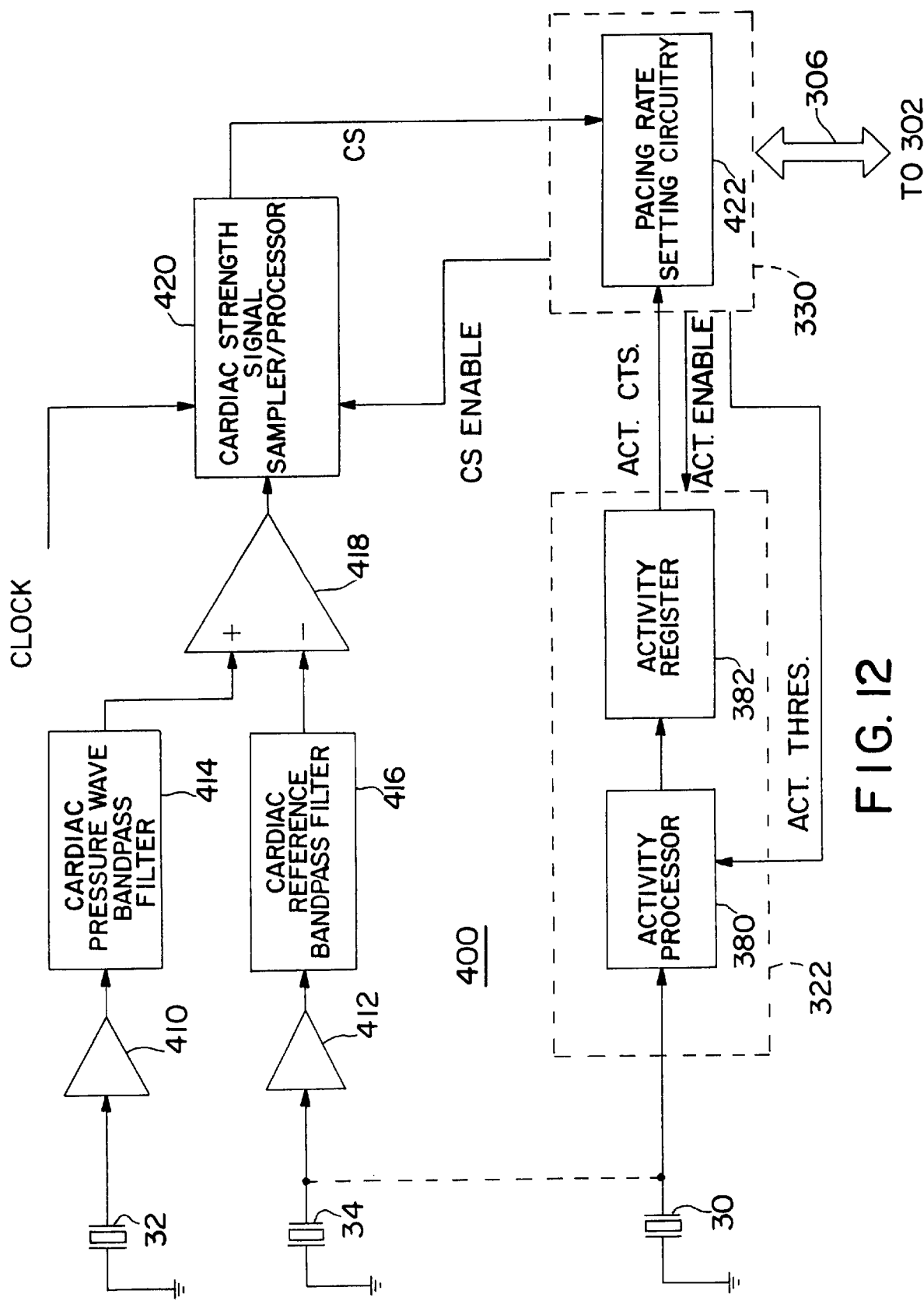
FIG. 12 is a block diagram of signal processing circuitry usable in the system of FIG. 11 for deriving a contraction strength physiologic signal and (optionally) an activity count physiologic signal related to the metabolic demand for cardiac output.

Turning to FIGS. 10 and 12, the activity count signal is derived in activity circuit 322 in the a conventional manner. The activity signal processing circuit 322 is shown coupled to the activity sensor 30, and the alternative preferred connection with the reference transducer 34 is shown in dotted line. The activity signal processing circuit 322 includes an activity processor 380 which amplifies and bandpass filters the transducer or sensor generated activity signal to exclude all signal frequencies outside the footfall band. For example, the piezoelectric transducers as described above are sensitive to heart contraction and respiration sound or motion frequencies of interest as well as to footfalls when the patient is ambulatory, muscle artifacts or myopotentials associated with limb movements and exercise, and may be responsive to speech and exterior environmental noise. All of these frequency and amplitude components except those characteristic of patient footfalls constitute "noise" in the activity channel that are first filtered out to the extent possible. In sensing patient footfalls to provide an accurate activity signal, the bandpass frequency range of interest is between about 0.5–15 Hz.

Peaks in the bandpass-filtered activity signal which exceed a predetermined threshold are interpreted by activity processor 380 as an indication of patient activity of sufficient magnitude to be included as an activity count. The predetermined threshold, which may be among the programmably selectable parameters of IPG 300, is also intended to screen out background "noise" in the sensor output signal indicative of low patient activity, or of other physical stresses which are not actually indicative of patient ambulatory movement.

Each occurrence of a peak in the bandpass-filtered sensor signal which exceeds the predetermined threshold is designated an ACT. CTS. A sum of ACT. CTS., maintained in an activity register 382 in digital controller/timer circuit 322, is computed over a predetermined period of time, e.g., over two second intervals. In accordance with the presently disclosed embodiment of the invention, two-second ACT. CTS. sums are provided, via I/O lines, to pacing rate setting circuitry 422 in digital controller/timer circuit 330. The concept of deriving, from a piezoelectric element, an ACT. CTS. representative of the level of a patient's physical activity, is well known and understood in the prior art, as exemplified by the above-incorporated '813 application or in the '927, '813 and '388 patents, and will thus not be described herein in additional detail. It is believed that those of ordinary skill in the art will be familiar with utilization of a piezoelectric sensor to perform activity sensing in an activity-responsive cardiac pacing and will be readily able to implement such a capability in a manner suitable for the purposes of practicing the present invention.

In FIGS. 9 and 10, the pressure wave signal provided by the pressure wave transducer 32 (either 32A or 32V, if both are present) is amplified in amplifier 510 and bandpass filtered in bandpass filter 514. The amplified and filtered respiration pressure wave is applied to one input of differential amplifier 518. Similarly, the reference pressure wave signal provided by the reference transducer 34 or the activity sensor 30 is amplified in amplifier 512 and bandpass filtered in bandpass filter 516. The amplified and filtered reference wave is applied to the other input of differential amplifier 518. To exclude other signals from this channel and to detect the frequency of the respiratory signal depicted in FIG. 8, the bandpass frequency is set to between 0.05–0.8 Hz.

The differential amplifier 518 removes any common mode noise in the respiratory frequency range of interest, and the output signal of interest is applied to the respiratory signal sampler/processor 520. The respiratory signal sampler/processor 520 is enabled by the RSP ENABLE signal from the digital controller/timer 330 when the respiratory signal is a programmed RCP. The respiratory signal sampler/processor 520 then provides at least the respiratory minute ventilation count signal MV CTS. and optionally a respiratory rate RR signal to the pacing rate setting system 422 in the digital controller/timer 330.

The respiratory signal sampler/processor 520 includes pressure wave signal processing circuitry for determining the respiratory physiologic signal related to the metabolic demand for cardiac output from the frequency and amplitude components of the pressure wave signal. As described above, a lead body pressure wave caused by lead body motion due to expansion and contraction of the patient's pleural cavity and chest with breathing exhibits distinctive frequency and amplitude components. The pressure wave signal processing circuitry within respiratory signal sampler/processor 520 peak detects the amplitude component and provides the R.R signal as a function of the breathing rate. The amplitude variation is sampled to derive the TV, and respiratory minute ventilation $E_V$ is determined in terms of the MV CTS output from respiratory signal sampler/processor 520. The development of these signals may be accomplished in employing a delta modulator in accordance with the teachings of the above-incorporated '253 patent and '813 application.

Pacing rate setting circuitry 422 can be programmed to respond to the MV CTS. signal alone or in combination with the ACT. CTS. signal to determine a pacing rate to meet the metabolic demand for cardiac output in a manner described in the above-incorporated '813 application or the '170 and '524 patents. Pacing rate setting circuitry 422 can also be programmed to respond to the RR signal alone or in combination with the ACT. CTS. signal to determine a pacing rate to meet the metabolic demand for cardiac output in a manner described in the '927 patent, incorporated herein by reference.

In FIGS. 11 and 12, the pressure wave signal provided by the pressure wave transducer 32 (either 32A or 32V, if both are present) is amplified in amplifier 410 and bandpass filtered in bandpass filter 414. The amplified and filtered respiration pressure wave is applied to one input of differential amplifier 418. Similarly, the reference pressure wave signal provided by the reference transducer 34 or the activity sensor 30 is amplified in amplifier 412 and bandpass filtered in bandpass filter 416. The amplified and filtered reference wave is applied to the other input of differential amplifier 418. To exclude other signals and detect the frequency of the contraction strength signals depicted in FIGS. 6 and 7, the bandpass frequency is set to between 0.5–7.0 Hz in the atrium and in the ventricle.

The differential amplifier 418 removes any common mode noise in the frequency range of interest, including any contribution due to patient footfalls, and the output signal of interest is applied to the contraction strength signal sampler/processor 420. The contraction strength signal sampler/processor 420 is enabled by the C.S. ENABLE signal from the digital controller/timer 330 when the contraction strength signal is a programmed RCP. The contraction strength signal sampler/processor 420 then provides at least the contraction strength signal C.S. to the pacing rate setting system 422 in the digital controller/timer 330.

The contraction strength signal sampler/processor 420 includes pressure wave signal processing circuitry for determining the contraction strength physiologic signal related to the metabolic demand for cardiac output from the frequency and amplitude components of the pressure wave signal. As described above, a lead body pressure wave caused by lead body motion due to expansion and contraction of the patient's heart and/or filling and emptying of the chambers thereof with each heart beat exhibits distinctive frequency and amplitude components. The pressure wave signal processing circuitry within contraction strength signal sampler/processor 420 samples the amplitude variations and provides the C.S. signal as a function of the peak amplitude. The variations of peak amplitude from a norm for a given intrinsic heart rate or pacing rate may be employed as the C.S. signal in a manner analogous to the processing of the blood pressure signal in the above-incorporated '170 patent.

Pacing rate setting circuitry 422 responds to either or both of the C.S. signals alone or in combination with the ACT. CTS. signal to determine a pacing rate to meet the metabolic demand for cardiac output in a manner described in the above-incorporated '170 patent.

Turning now to FIG. 13, it depicts a third dual chamber pacemaker embodiment in which the invention is preferably implemented for providing rate-responsive pacing as a function of one or more of the RR, MV CTS. ACT. CTS. and C.S. physiologic signals derived in accordance with the circuitry of FIGS. 10 and 12. In addition, the use of the reference transducer 34 to derive the ACT. CTS. value is also depicted. It will be understood that the physiologic signals may be derived using only one of the depicted pressure wave transducers 32A, 32V. It will be further understood that the selected signal values may be used alone or in combination as described above.

The illustrated IPG block diagrams of FIGS. 9, 11 and 13 are merely exemplary, and correspond to the general functional organization of most multi-programmable microprocessor controlled DDD(R) cardiac pacemakers presently commercially available. It is believed that the present invention is most readily practiced in the context of such a device, and that the present invention can therefore readily be practiced using the basic hardware of existing microprocessor controlled dual chamber pacemakers, as presently available, with the invention implemented primarily by means of modifications to the software stored in the ROM 312 of the microcomputer circuit 302. However, the present invention may also be usefully practiced by means of a full custom integrated circuit, for example, a circuit taking the form of a state machine in which a state counter serves to control an arithmetic logic unit to perform calculations according to a prescribed sequence of counter controlled steps. As such, the present invention should not be understood to be limited to a pacemaker having an architecture as illustrated in FIGS. 9, 11 and 13, and a circuit architecture as illustrated in FIGS. 9, 11, and 13 is not believed to be a prerequisite to enjoying the benefits of the present invention.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

PARTS LIST FOR FIGS. 1–13

IPG 10
patient's chest 12
heart 14
distal end segment 16
endocardial lead 18
atrial lead 18A
ventricular lead 18V
atrial electrodes 19, 21
connector assembly 20
case or can 22
ventricular electrodes 23, 25
lungs 24, 26
diaphragm 28
activity sensor 30
pressure wave transducer 32
atrial pressure wave transducer 32A
ventricular pressure wave transducer 32V
piezoelectric crystal 33, 39 reference transducer 34
thin film electrode 35, 37, 41, 43
connector housing 36
lead connector end bore 38
proximal connector end 40
tubular end 42
pin receptacle chamber 44
cavity 45
tubular end extension 46
access port 47
flexible sleeve 48
in-line lead retainers 50, 52
lumen 54
proximal connector pin 56
annular moisture sealing ribs 58
connector ring 60
annular moisture sealing ribs 62
diameter 64
insulating layer 65
annular groove 66
suture ring 68
cavities 70, 71
double pin reference feedthrough 72
lead feedthrough 74, 78
double pin pressure wave feedthrough 76
lead feedthrough pin 80, 82
reference feedthrough pin 84, 86
welding ports 87 and 89
pressure wave feedthrough pin 88, 90
opening 92
enlarged section 96, 98
leaf spring 100
accelerometer 102
accelerometer leads 104, 106
IPG circuit 300
microcomputer circuit 302
microprocessor 304
data and control bus 306
system clock 308
on-processor RAM chip 310
on-processor ROM chip 312
RAM/ROM unit 314
activity sensor 316
battery 318
input/output circuit 320
activity circuit 322
activity signal 324
reference mode circuit 326
ADC and multiplexor circuit 328
digital controller/timer circuit 330
RF transmitter and receiver circuit 332
telemetry antenna 334
power-on-reset circuit 336
crystal oscillator circuit 338
pace output amplifier circuit 340
V-TRIG line 342
A-TRIG line 344
pace energy control 348
capture detect circuit 350
A-EVENT line 352
V-EVENT line 354
sense amplifier 360
activity processor 380
activity register 382
pacing rate setting circuitry 390
contraction strength signal processor 400
contraction strength amplifiers 410, 412
contraction strength bandpass filters 414, 416
contraction strength differential amplifier 418
contraction strength signal sampler/processor 420
respiration signal processor 500
respiration amplifiers 510, 512
respiration bandpass filters 514, 516
respiration differential amplifier 518
respiratory signal sampler/processor 520
pressure wave signal processor 600

What is claimed is:

1. In a rate-responsive cardiac pacemaker, a system for deriving a physiologic signal related to the metabolic demand for cardiac output as a function of pressure waves within the patient's body and deriving a pacing rate control signal therefrom for setting a pacing rate to satisfy the metabolic demand for cardiac output comprising:

an elongated pacing lead comprising:
an elongated lead body extending between a proximal connector end and a distal end adapted to be placed in association with the heart and adapted to conduct body pressure waves to the proximal connector end thereof;
a pace/sense electrode at the distal end of said lead body; and
a pace/sense lead conductor within said lead body extending between said proximal connector end and said pace/sense electrode for conducting pacing pulses from said proximal connector end to said pace/sense electrode and for conducting electrogram heart signals from said pace/sense electrode to said proximal connector end; and a cardiac pacemaker pulse generator comprising:
a connector assembly for attachment with said proximal connector end;
a pressure wave transducer mounted in said connector assembly in relation to said proximal connector end for detecting said pressure wave through said lead body using a solid mechanical linkage to said transducer and for providing a pressure wave signal;
pressure wave signal processing means responsive to said pressure wave signal for determining a physiologic signal related to the metabolic demand for cardiac output;
rate setting means responsive to said physiologic signal for determining a pacing rate to meet the metabolic demand for cardiac output; and
a pulse generator for generating and delivering a pacing pulse through said connector assembly and said proximal connector end connected thereto to said pace/sense electrode at said pacing rate.

2. The system of claim 1 wherein:
said pressure wave transducer is responsive to lead body pressure waves reflecting lead body motion caused by the contraction of the patient's heart and provides said pressure wave signal having contraction frequency and amplitude components representative thereof; and
said pressure wave signal processing means provides a heart contraction strength signal in response to said contraction frequency and amplitude components of said physiologic signal.

3. The system of claim 1 wherein:
said pressure wave transducer is responsive to lead body pressure waves reflecting lead body motion caused by the breathing of the patient and provides a pressure wave signal having respiration frequency and amplitude components representative thereof; and said pressure wave signal processing means provides a respiration rate signal in response to said respiration frequency and amplitude components of said physiologic signal.

4. The system of claim 1 wherein:
said pressure wave transducer is responsive to lead body pressure waves reflecting lead body motion caused by the breathing of the patient and provides a physiologic pressure wave signal having respiration frequency and amplitude components representative thereof; and said pressure wave signal processing means provides a respiratory minute ventilation signal from the respiration frequency and amplitude components of said physiologic pressure wave signal.

5. The system of claim 1 wherein said pressure wave detection transducer comprises a miniaturized accelerometer.

6. The system of claim 1 further comprising:
a reference transducer mounted in said connector assembly and isolated from said proximal connector end for detecting common mode noise signals and providing a reference signal in response thereto; and
means for processing said signal and said pressure wave signal for removing common mode noise and detecting pressure waves associated with said body site.

7. The system of claim 6 wherein said pressure wave detection transducer is affixed within said connector assembly so as to be adapted and disposed to ensure direct physical contact with said proximal connector end, for the transfer of said pressure waves through said direct physical contact.

8. The system of claim 1 wherein:
said pressure wave transducer is responsive to lead body pressure waves reflecting lead body motion caused by the activity of the patient and provides a pressure wave signal having activity frequency and amplitude components representative thereof; and
said pressure wave signal processing means provides an activity signal in response to said activity frequency and amplitude components of said pressure wave signal of said physiologic signal.

9. The system of claim 8 further comprising a reference transducer isolated from mechanical linkage to said lead body.

10. The system of claim 9 wherein said pressure wave detection transducer and said reference transducer are piezoelectric crystal transducers.

11. In a rate-responsive cardiac pacemaker, a system for deriving a pacing rate control signal from physiologic signals related to the metabolic demand for cardiac output for setting a pacing rate to satisfy the metabolic demand for cardiac output comprising:
an elongated pacing lead comprising:
an elongated lead body extending between a proximal connector end and a distal end adapted to be placed in association with the heart and adapted to conduct body pressure waves to the proximal connector end thereof;
a pace/sense electrode at the distal end of said lead body; and
a pace/sense lead conductor within said lead body extending between said proximal connector end and said pace/sense electrode for conducting pacing pulses from said proximal connector end to said pace/sense electrode and for conducting electrogram heart signals from said pace/sense electrode to said proximal connector end; and a cardiac pacemaker pulse generator comprising:
a connector assembly for attachment with said proximal connector end;
a pressure wave transducer mounted in said connector assembly and attached through a solid mechanical linkage to said proximal connector end for detecting said pressure wave and providing a pressure wave signal;
pressure wave signal processing means responsive to said pressure wave signal for determining a first physiologic signal related to the metabolic demand for cardiac output;
activity sensing means for sensing patient activity pressure waves and providing an activity signal;
activity signal processing means responsive to said activity signal for determining a second physiologic signal related to the activity related metabolic demand for cardiac output;
rate setting means responsive to the first and second physiologic signals for determining a pacing rate to meet the metabolic demand for cardiac output; and
a pulse generator for generating and delivering a pacing pulse through said connector assembly and said proximal connector end connected thereto to said pace/sense electrode at said pacing rate.

12. The system of claim 11 wherein:
said pressure wave transducer is responsive to lead body pressure waves reflecting lead body motion caused by the contraction of the patient's heart and provides said pressure wave signal having contraction frequency and amplitude components representative thereof;
said pressure wave signal processing means provides a heart contraction strength signal in response to said contraction frequency and amplitude components; and
said rate setting means is responsive to said heart contraction strength signal and said second physiologic signal for determining the pacing rate.

13. The system of claim 11 wherein:
said pressure wave transducer is responsive to lead body pressure waves reflecting lead body motion caused by the breathing of the patient and provides a pressure wave signal having respiration frequency and amplitude components representative thereof;
said signal processing means provides a respiration rate signal in response to said respiration frequency and amplitude components; and
said rate setting means is responsive to said respiration rate signal and said second physiologic signal for determining the pacing rate.

14. The system of claim 11 wherein:
said pressure wave transducer is responsive to lead body pressure waves reflecting lead body motion caused by the breathing of the patient and provides a pressure wave signal having respiration frequency and amplitude components representative thereof;
said signal processing means provides a respiratory minute ventilation signal from the respiration frequency and amplitude components of the pressure wave; and
said rate setting means is responsive to said respiratory minute ventilation signal and said second physiologic signal for determining the pacing rate.

15. In a rate-responsive cardiac pacemaker, a system for deriving a pacing rate control signal from physiologic signals related to the metabolic demand for cardiac output for setting a pacing rate to satisfy the metabolic demand for cardiac output comprising: an elongated pacing lead comprising: an elongated lead body to be placed in association with the heart and adapted to conduct body pressure waves to the proximal connector end thereof; a pace/sense electrode at the distal end of said lead body; and a pace/sense lead conductor within said lead body extending between a proximal connector end and a distal end adapted extending between said proximal connector end and said pace/sense electrode for conducting pacing pulses from said proximal connector end to said pace/sense electrode and for conducting electrogram heart signals from said pace/sense electrode to said proximal connector end; and a cardiac pacemaker pulse generator comprising: a connector assembly for attachment with said proximal connector end; a pressure wave transducer mounted in said connector assembly and being in mechanical linkage to said proximal connector end for detecting said pressure wave and providing a pressure wave as transmitted by said lead body signal; ressure wave signal processing means responsive to said pressure wave signal for determining a first physiologic signal related to the metabolic demand for cardiac output; activity sensing means for sensing patient activity pressure waves and providing an activity signal; said activity signal processing means is responsive to said activity frequency and amplitude components of said activity signal for providing said second physiologic signal; rate setting means responsive to the first and second physiologic signals for determining a pacing rate to meet the metabolic demand for cardiac output; and a pulse generator for generating and delivering a pacing pulse through said connector assembly and said proximal connector end connected thereto to said pace/sense electrode at said pacing rate.

* * * * *